US010540481B2

(12) United States Patent
Shah

(10) Patent No.: US 10,540,481 B2
(45) Date of Patent: Jan. 21, 2020

(54) SYSTEM AND METHODS FOR IMPROVED PHARMACEUTICAL ACCURACY AND UNDERSTANDING

(71) Applicant: My Meds, Inc., Minneapolis, MN (US)

(72) Inventor: Rajiv R. Shah, Minneapolis, MN (US)

(73) Assignee: My Meds, Inc., Minneapolis, MN (US)

( * ) Notice: Subject to any disclaimer, the term of this patent is extended or adjusted under 35 U.S.C. 154(b) by 81 days.

(21) Appl. No.: 14/058,788

(22) Filed: Oct. 21, 2013

(65) Prior Publication Data

US 2014/0278482 A1 Sep. 18, 2014

Related U.S. Application Data

(60) Provisional application No. 61/783,846, filed on Mar. 14, 2013.

(51) Int. Cl.
*G06Q 50/00* (2012.01)
*G06F 19/00* (2018.01)
*G09B 19/00* (2006.01)
*G06Q 10/00* (2012.01)

(52) U.S. Cl.
CPC ......... *G06F 19/3456* (2013.01); *G09B 19/00* (2013.01)

(58) Field of Classification Search
CPC ........ G06Q 50/22; G06Q 50/24; G06Q 10/10; G06Q 40/08; A61N 1/08; G06F 17/30; G06F 19/30; G06F 19/32; G06F 19/321; G06F 19/324; G06F 19/325; G06F 19/326; G06F 19/328; G06F 19/34; G06F 19/3418; G06F 19/3456; G06F 19/3462; G06F 19/3468; G06F 19/3475; G06F 19/3481; G06F 19/36; G16H 10/00; G16H 10/20; G16H 10/40; G16H 10/60; G16H 10/65; G16H 15/00; G16H 20/00; G16H 20/10; G16H 20/13; G16H 20/17; G16H 20/30; G16H 20/40; G16H 20/60; G16H 20/70; G16H 20/90; G16H 30/00; G16H 30/20; G16H 30/40; G16H 40/00; G16H 40/20; G16H 40/40; G16H 40/60; G16H 40/63; G16H 40/67; G16H 50/00; G16H 50/20; G16H 50/30; G16H 50/50; G16H 50/70; G16H 50/80; G16H 70/00; G16H 70/20; G16H 70/14; G16H 70/60; G16H 80/00
USPC ........................................................ 705/2–3
See application file for complete search history.

(56) References Cited

U.S. PATENT DOCUMENTS 5,737,539 A * 4/1998 Edelson et al. ................... 705/3
5,758,095 A * 5/1998 Albaum et al. ................... 705/2
5,845,255 A * 12/1998 Mayaud ............................ 705/3
6,046,761 A * 4/2000 Echerer ...................... 348/14.01
(Continued)

*Primary Examiner* — Victoria P Augustine
(74) *Attorney, Agent, or Firm* — Schwegman Lundberg & Woessner, P.A.

(57) ABSTRACT

The present disclosure in some embodiments relates to a computer-based method for improving the pharmaceutical understanding of a user. The method includes receiving medication data from a source, wherein the medication data is related to a user's prescribed, dispensed, or claimed medicines; associating a unique ID for each user with the medication data for the user; providing a user interface, whereby the data for a user is accessible to the user only after the user has provided an authentication, wherein the medication data accessible to the user via the user interface comprises the one or more medications the user is taking.

18 Claims, 25 Drawing Sheets

(56) References Cited

U.S. PATENT DOCUMENTS

| | | | |
|---|---|---|---|
| 7,072,840 B1* | 7/2006 | Mayaud | 705/2 |
| 7,454,880 B1* | 11/2008 | Austin et al. | 53/411 |
| 7,483,839 B2* | 1/2009 | Mayaud | 705/2 |
| 7,519,540 B2* | 4/2009 | Mayaud | 705/2 |
| 7,574,370 B2* | 8/2009 | Mayaud | 705/3 |
| 7,606,723 B2* | 10/2009 | Mayaud | 705/2 |
| 8,249,897 B2* | 8/2012 | Yamaga et al. | 705/3 |
| 8,494,880 B2* | 7/2013 | Tripoli | 705/3 |
| 2006/0031101 A1* | 2/2006 | Ross | 705/3 |
| 2008/0283542 A1* | 11/2008 | Lanka et al. | 221/6 |
| 2012/0040319 A1* | 2/2012 | Brackett et al. | 434/262 |
| 2012/0173319 A1* | 7/2012 | Ferrara | 705/14.4 |
| 2013/0063579 A1* | 3/2013 | Hanina et al. | 348/61 |
| 2013/0079924 A1* | 3/2013 | Garda et al. | 700/236 |

\* cited by examiner

Welcome to MyMeds

MYMEDS

Create, Track & Share Medication Records for the Whole Family!

It is proven that people who understand and track their medications are healthier. Managing your medications well prevents hospitalizations, frequent visits to the doctor, and worsening of chronic conditions like diabetes, heart failure and kidney disease. By using MyMeds, you are taking charge of an important aspect of your health.

MyMeds allows you to:
- Create medication profiles for up to 16 people
- Keep track of all your meds: prescription, over-the-counter, vitamins, and supplements
- Share your records with whoever you choose, including your doctors and caregivers
- Easily view and edit your records no matter where you are
- Rest assured that your medication records are securely and privately held in HIPPA-compliant cloud storage Complete the Create Account form on this page to get started.

If you already have an account Sign In
Did you forget your password?

Create your MyMeds account — 210

| First Name: | jenna |
| Last Name: | Lane |
| Email Address*: | jennalane@outlook.com |
| Confirm Email Address*: | jennalane@outlook.com |
| Password*: | ******* |
| Confirm Password*: | ******* |

☑ You Accept our Term of Service

Answer*: What is your favorite sport? ▲▼
soccer

*Required fields

[CREATE ACCOUNT]

[CONTACT MYMEDS]

About MyMeds | Privacy Policy | Terms Of Service

MYMEDS

Logged in as Jenna Lane  MyMeds Points 1: (What's this?)  MY ACCOUNT  LOGOUT — 233

— 200

Jenna Lane ▾ | ADD | EDIT — 212

Jenna Lane

— 214

Personal Information ➤ — 216
Primary Doctor ➤ — 218
Primary Pharmacy ➤ — 220

INVITE

EMAIL | PRINT | TEXT | CARD

MEDICATION TRACKING

MEDICATIONS — 224 | DRUG ALLERGIES — 226 | DOCTORS — 228 | PHARMACIES — 230 | NOTES — 232

Doctors   •ADD NEW — 234                    Text size A A A

| Doctor Name | Primary | Clinic Name | Address | Phone | Specialty |
|---|---|---|---|---|---|
| Rahimi, Amir | Primary | Consultants Internal Medicine, PA | 15 Red Berry Road, M.... | (952)555-8181 | Internal Medicine |
| Haval, Doris | Make Primary | Minneapolis Endocrinology | 1 Splendor Court, M.... | (612)555-2500 | Endocrinology (Diabetes) |
| Jaynes, William | Make Primary | Cardiology Specialties | | (612)555-8000 | Cardiology |
| Werier, Michael | Make Primary | Allergy & Immunology Consultants | | (952)555-1010 | Allergy/Immunology |

— 236

2011 MyMeds, Inc - All Rights Reserved - Privacy Policy | Terms Of Service | Hide

CONTACT MYMEDS

WhyMeds

*Medication  [Lisinopril 20mg Tab]

*Reason for taking  [high blood pressure]

[Enter or Select from List
congestive heart failure
high blood pressure
kidney protection
(Not Sure)]

Quantity  [1 table]
Start Date  [04/21]

Special Instructions/Notes
☐ Do not take with milk.
☐ Do not take with alcohol.
☑ Take with food.
☐ Do not take with food.
☐ Other

Fig. 2G

Edit Medication

[Emma Long ▼] [ADD] [EDIT]

Emma Longwell

Personal Information ▶
Primary Doctor ▶
Primary Pharmacy ▶

INVITE

WhyMeds

Not sure? Contact your doctor or pharmacist to learn why you take this medication

[kidney protection]
Not Sure

Start Date  [04]

Special Instructions/Notes
☐ Do not take with milk.

MyMeds Medication Profile for Jenna Lane

From: jennalane@my-meds.com
To: diana@my-meds.com
Date: 05-18-2013 03:19 PM

MYMEDS

MyMeds Medication Profile
for Jenna Lane

Date of Birth: 05/10/1972
Phone: (612)207-1014
Email: jennalane@outlook.com

Current Medications

| Medication | Reason | Quantity | Frequency |
|---|---|---|---|
| Aspirin 81mg Tab | blood thinner | 1 tablet | once a day |
| Fish Oil + D Softgel | Not sure* | 1 softgel | once a day |
| Lantus 100units/ml Soln for inj | diabetes | Not Applicable | at bedtime |
| Lipitor 10mg Tab | high cholesterol | 1 1/2 tablets | once a day |
| Motrin IB 200mg Caplet | pain/inflammation | 1 tablet | As Needed |
| Zantac 150mg Tab | acid reflux | 1 tablet | once a day |
| Zyrtec 10mg Tab | allergies | 1 tablet | once a day |

*Not sure? Contact your doctor or pharmacist to learn why you take this medication!

Drug Allergies
| Medication | Allergic Reaction |
|---|---|
| Ketorolac 10mg Tab | Rapid Heartbeat |
| Penicillin G 20mil U Pwd for inj | Rash |

MyMeds, inc 2013

| Carrier 🛜 3:59 PM |
|---|
| [Back] Doctor Details |
| Name: Rahimi, Amir |
| Clinic: Consultants Internal Medicine, P.A. |
| Specialty: Internal Medicine |
| Phone: (952)555-8181 |
| Address: 15 Red Berry Road, Minneapolis, MN, US, 55920 |
| Visit MyMeds.com to edit Doctor info |

Fig. 3M

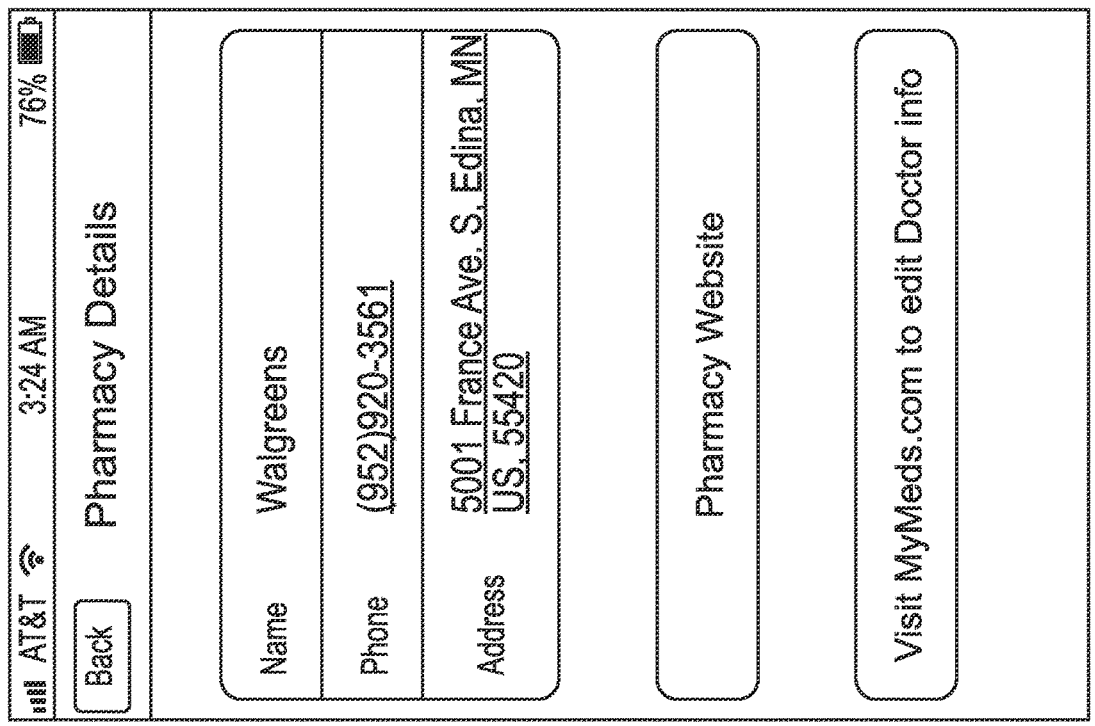

SYSTEM AND METHODS FOR IMPROVED PHARMACEUTICAL ACCURACY AND UNDERSTANDING

CROSS-REFERENCE TO RELATED APPLICATIONS

This application claims priority to U.S. Provisional Application No. 61/783,846, entitled, "System and Methods for Improved Pharmaceutical Accuracy and Understanding," filed Mar. 14, 2013, which is hereby incorporated herein in its entirety.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Because our current healthcare system is not a holistic system, but rather is one that may include a patient seeing two or more doctors or specialists that do not always communicate with one another, it is difficult for many people to feel as though they have a handle on their health care. This problem may be particularly pronounced and concerning as it relates to prescription drugs. Because people, particularly sick and/or elderly people, may have more than one doctor prescribing drugs for them, it is more important than ever to monitor one's own prescription drug use rather than relying on one or more other people. However, current methods of obtaining information about and/or tracking and/or managing one's prescription drug use may be too complicated, too time consuming, or too expensive. There is therefore a need for a user-friendly, easy, informative way to manage one's prescription drug use.

BRIEF SUMMARY OF THE INVENTION

The following presents a simplified summary of one or more embodiments of the present disclosure in order to provide a basic understanding of such embodiments. This summary is not an extensive overview of all contemplated embodiments, and is intended to neither identify key or critical elements of all embodiments, nor delineate the scope of any or all embodiments.

The present disclosure in some embodiments relates to a computer-based method for improving the pharmaceutical understanding of a user. The method includes receiving medication data from a source, wherein the medication data is related to a user's prescribed, dispensed, or claimed medicines; associating a unique ID for each user with the medication data for the user; providing a user interface, whereby the data for a user is accessible to the user only after the user has provided an authentication, wherein the medication data accessible to the user via the user interface comprises the one or more medications the user is taking.

In some embodiments, the user may be an employee. In some embodiments, the source may be the user's employer. In some embodiments, the source may be the user's insurer or pharmacy benefit manager. The source may be a pharmacy in other embodiments.

In some embodiments, the medication data may be prescription medicines, over-the-counter medicines, vitamins, and herbal supplements.

In some embodiments, the method may include alerting the user via the user interface if two or more of the medications the user is taking are contra-indicated.

A user tutorial may also be provided that associates the one or more medications the user is taking with the reason the medication is being taken, in some embodiments.

Medication data may be received from a source in substantially real-time in some cases. In other embodiments or in addition to real-time, the receiving of medication data from a source may be completed over pre-determined intervals of time.

In some embodiments the user may grant one or more other entities access to the user's medication data. In some cases, the access granted may be view-only access. In other cases, the access may be view-and-edit access. The method may also include providing the user with alerts indicating when one or more medications the user is taking need to be refilled.

The present disclosure in some embodiments includes a method for managing one or more medications taken by a user. The method includes receiving medication data from a user's employer, wherein the medication data is related to a user's prescribed, or claimed medicines. A unique ID may be associated with each user with the medication data for the user. A user interface may also be provided, whereby the data for a user is accessible to the user only after the user has provided an authentication, wherein the medication data accessible to the user via the user interface comprises the one or more medications the user is taking; and providing a rewards system the user accesses from the user interface.

In some embodiments, the reward system includes giving a user points for successfully completing one or more tasks. In some embodiments, the data received from the user's employer is from an employer-based insurer.

The present disclosure in other embodiments includes a method for managing one or more medications taken by a user. The method includes, receiving medication data from a source, wherein the medication data is related to a user's prescribed, dispensed, and claimed medicines; associating a unique ID for each user with the medication data for the user; providing a user interface, whereby the data for a user is accessible to the user only after the user has provided an authentication; and providing a tutorial that the user may access form the user interface, wherein the tutorial associates the reason for taking a medication with the name of the medication.

In some embodiments, the source is an employer of the user. In other embodiments, the source is the user.

While multiple embodiments are disclosed, still other embodiments of the present disclosure will become apparent to those skilled in the art from the following detailed description, which shows and describes illustrative embodiments of the disclosure. As will be realized, the various embodiments of the present disclosure are capable of modifications in various obvious aspects, all without departing form the spirit and scope of the present disclosure. Accordingly, the drawings and detailed description are to be regarded as illustrative in nature and not restrictive.

BRIEF DESCRIPTION OF THE DRAWINGS

In the accompanying drawings, reference characters refer to the same parts throughout the different figures. The drawings are not necessarily to scale, emphasis has instead been placed upon illustrating the principles of embodiments of the present disclosure. With respect to the drawings.

DETAILED DESCRIPTION

Figure 1:
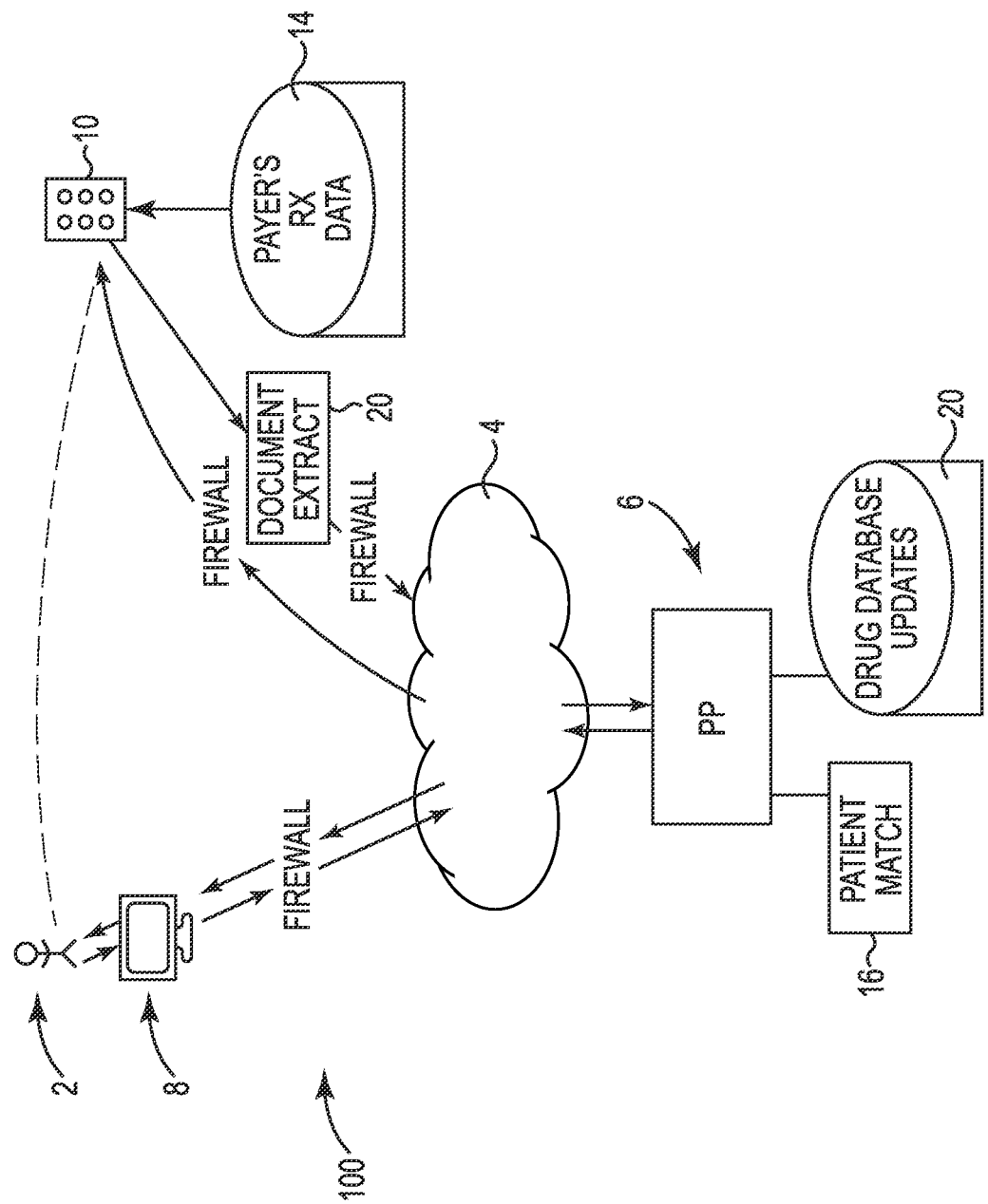
FIG. 1 is a diagram showing an system of the present disclosure, in accordance with one embodiment.

The present disclosure in some embodiments is directed to systems and methods for increasing pharmaceutical competency of patients, by providing users/patients with a location to track, manage, learn about, and improve their understanding of the one or more medications they may be taking. In some embodiments the systems of the present disclosure may be a web-based system. In some cases, the web-based system may be managed by a Portal Provider. In at least one embodiment of the present disclosure, the health tracking system and methods 100 described herein utilize a cloud-based 4 system managed by a Portal Provider 6 with a web-based user interface 8, 10, which may be a multi-channel method, as shown in FIG. 1.

In some embodiments, a user may be an individual user not associated with an employer. In other embodiments, the user 2 may be an employee of a company 10, as shown in FIG. 1. A user in some embodiments may enroll directly for services with the Portal Provider System ("PPS") via a web-based user interface, the telephone, mail-in materials, etc. In other embodiments, the user's enrollment may be associated with and/or initiated by the user's employer. In some embodiments of employer-based systems, such as that shown in FIG. 1, the system 100 may generally be configured as follows: the company 10 may receive information related to prescription medication, for example, for each of its participating employees 2 directly from the payer's prescription data 14; before this information is transmitted to the PPS 6, the data may be processed through a secure data extraction process 20, such that only the desired and/or HIPAA-compliant information, for example, may be provided to the PPS 6; in some cases the user 2 may also provide the PPS 6 with their own medication information, as will be discussed further below; the PPS 6 may include a number of features and may have access to a plurality of databases—for example, the PPS 6 may include a patient match engine 16 that matches a user's registration information to drug information received from the payer prescription data, for example. In some embodiments, the PPS 6 may also include a drug database 20 that may be accessed by the system to provide the most current and up-to-date drug information for use by the system 100. The overall system 100 may be secured by one or more methods, including the use of encryption, password protection, firewalls, etc. Further, the overall system 100 may be complaint with all relevant and appropriate regulations, including for example HIPAA laws.

In some embodiments, the system and methods of the present disclosure may generally include the following steps: an employer may work together with the PPS to pre-populate the PPS with data related to the employer generally and/or with data related to each of its employee users of the system; the employer may also determine how future, on-going data will be provided to the PPS, including whether it will be provided in batch format, or in substantially real-time; the employer, employee, and/or the PPS may determine a unique employee identification number for each employee user; the PPS may include one or more databases with relevant and in some cases regularly updated information, such as pharmacy directories that include locations and contact information for pharmacies, drug databases that include drug information and images, medical dictionaries, medical encyclopedias, and/or any other useful information; the employee user may receive an invitation link from the PPS and/or the employer to register with the system; the employee may then register with the system including providing a secure password; the user interface of the system that may be made available to the user may include application that make available to the user all or some portion of the pre-populated data provided by the employer that has been matched to the specific user via the PPS patient matching engine; once registered and signed in, the user may access all of the advantageous features of the system described and disclosed herein.

As described above, in some embodiments the PPS may be pre-populated with data in a Data Pre-Population step (referred to herein as the "DPP" step). The DPP may be achieved a number of ways depending on the employer's preference, for example. In some embodiments, the employer and the Portal Provider System may work together to determine how the data upload will occur, including how frequently such uploads will occur. This coordination may take place in person, on-line, over the phone, or by any other suitable means. In some cases, the employee will interact with the PPS regarding the DPP through a secure web-based user interface. The employer may decide to provide the file data in one of several ways, including, but not limited to in a batch file, or a real-time transactional format.

A batch file may contain prescription history for all employees of the employer and may be delivered to the PPS on a consistent pre-determined frequency, in some embodiments. The employer and the PPS may also determine the secure file transfer method preferred for the upload. The DPP step may include the employer sending data via a secured transfer method. In some cases the data may include data obtained and/or stored over a pre-determined amount of time, for example, the previous twelve months. Though it will be understood that any appropriate time frame may be used. The specific data provided may include, but is not limited to medication data (e.g. medication name/strength/form, quantity, quantity unit, days' supply, instructions, refill information, written date, dispense/fill date, prescriber order number); prescribing physician information (e.g. NPI#, name, address, primary phone); pharmacy information (e.g. NCPDP ID, NPI, pharmacy name, address, primary phone); and individual information (e.g. employee unique ID, full name, date of birth, address).

The real-time transactional format may allow the PPS to request medication information for a particular employee/user/patient on an as-needed basis. In this case, the employer and PPS may determine the volume of data provided at each request. In use, a user may access the Portal Provider System, which may request medication history real time transaction data from the client. This process may involve, for example, retrieving the medication history claim or dispense data from the supplier's claim or dispense database.

In some cases the medication related information content may come directly from an insurer or pharmacy benefit manager, in which case the file upload will be via one of these third-parties and not directly through the employer. Though, it will be understood that in some cases, the employer may wish to be in control of what is uploaded to the PPS and therefore the employer may obtain information from the third party and then provide it to the Portal Provider System.

The employer may determine what data is made accessible related to the employee/user's medication history. Further, the employer may determine a unique identification for each employee. This identification may be any unique identification, such as, but not limited to a social security number, employee ID, or other identification. The employer may provide information for each of (or some subset of) its employees, including, but not limited to: unique ID for the employee; full name of employee; email address of employee; date of birth of employee; home address; and/or any other useful appropriate information. The employer may send the PPS an updated employee roster from time to time, and in some cases on a set schedule, for example, every six months, or 12 months. Any new employees may be added to the PPS and an invitation with a link may be sent to the new employee. The employer may update the Portal Provider System to indicate employees who leave the company, in some cases. Such employees may remain in the PPS system as individual users, but the user will no longer be associated with its former employer, in some cases.

The Portal Provider System ("PPS") may also include a complete and up-to-date pharmacy directory. In some embodiments, the directory may be obtained from the National Council for Prescription Drug Programs ("NCPDP"). The directory may allow the user to setup preferred pharmacies and may match to the medication histories dispensing pharmacy. The data in the directory may include, but is not limited to: NCPDP ID; National Provider Identification ("NPI"); pharmacy name; pharmacy address; pharmacy telephone number; pharmacy email. The PPS may include downloading the latest NCPDP pharmacy file on a regular basis, for example, in some embodiments, on a monthly basis. Though it will be understood that the information may be updated on an as-needed basis, a daily basis, a yearly basis, or any other suitable basis.

The PPS may also include a database including a complete drug file. In some cases, such a file may be provided by Gold Standard or other industry-standard database. The drug file may include drug name, images, uses, dosages, side-effects, contra-indications, etc. This file may be accessible to the user to assist the user by, for example, verifying the pre-loaded information and/or manually loading new or missing information manually into the PPS. The drug database vendor may send periodic updates to the PPS related to the drug database and images in an effort to always have the most current information available to the users of the PPS.

Once the DPP is complete, a user/employee may access the system. In some embodiments, the employer may send a registration link to each employee, by for example, hard copy mail, or electronic mail. In other cases, the PPS may send the link to the employee/user. The employee may receive an introductory email explaining the value of the PPS and a link that may allow the employee to register with the PPS. The employee may click on the link to arrive at a secure web site user interface page that may assist them through the registration process. The employee may create a user password, whereby the employee may not have access to the user's page without providing that password. While passwords are described, other authentication and security methods are also contemplated and within the spirit of the present disclosure. The employee/user may be asked to provide additional information such as demographic information, emergency information, or other relevant information. They may also be asked to review and verify the pre-populated information that includes the employee's medication information which may be linked up for viewing based on the employee's unique ID.

The user/employee may update their own user page with any new medications they may be taking. In at least one embodiment, the user can scan QR codes or UPC codes, for example, from the relevant new medications to update their medication data in the system. Alternately or additionally, the user's records may be automatically updated by or through their employer. The user/employee may be asked to verify any information that is automatically populated from a source other than the user/employee. In some embodiments, the user may manually archive medications they are no longer taking. If a new pharmacy is used, the system may be updated to reflect this. In some cases, the employer may provide the PPS with information obtained through claims data, thus each prescription filled through an employer's employer-based insurance may be provided to the PPS.

A user interface may be provided that is intuitive and user friendly. Many embodiments are contemplated and within the scope of the present disclosure. For example, an image of the shelves of a medicine cabinet may be seen, with bottles sitting on the shelf indicating each of the different medications that the patient may be taking. The bottle may have the name (generic and/or branded) of the drug on the front of the bottle. When the user scrolls over the image, an exploded view may appear that provides an image of the drug, the fill date, the dosage, the frequency of use, etc. Of course, other embodiments may include other ways of presenting the information. In some embodiments, the user may select between a number of different user interfaces. For example, in some embodiments, the interface may have an option for a recording to play the name of the drug, and other information related to the medicines a patient is taking and/or interested in, which may be particularly helpful for those with poor eye sight. In some embodiments, additional information may be made available to the curious user. For example, recent articles related to the medicine that is being taken and/or alternatives to the medicine may be made available to the user.

Figure 2B:
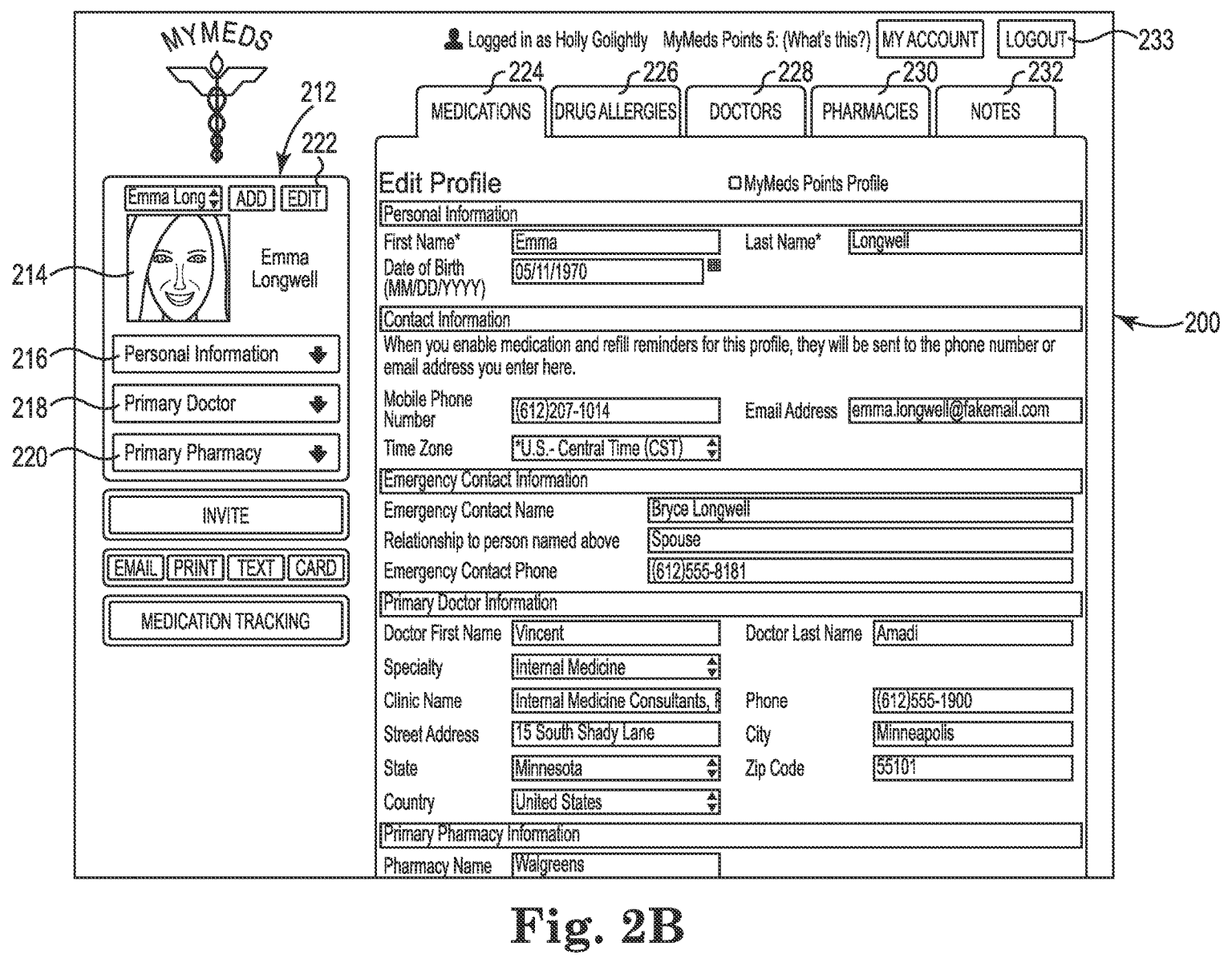
Figure 2D:
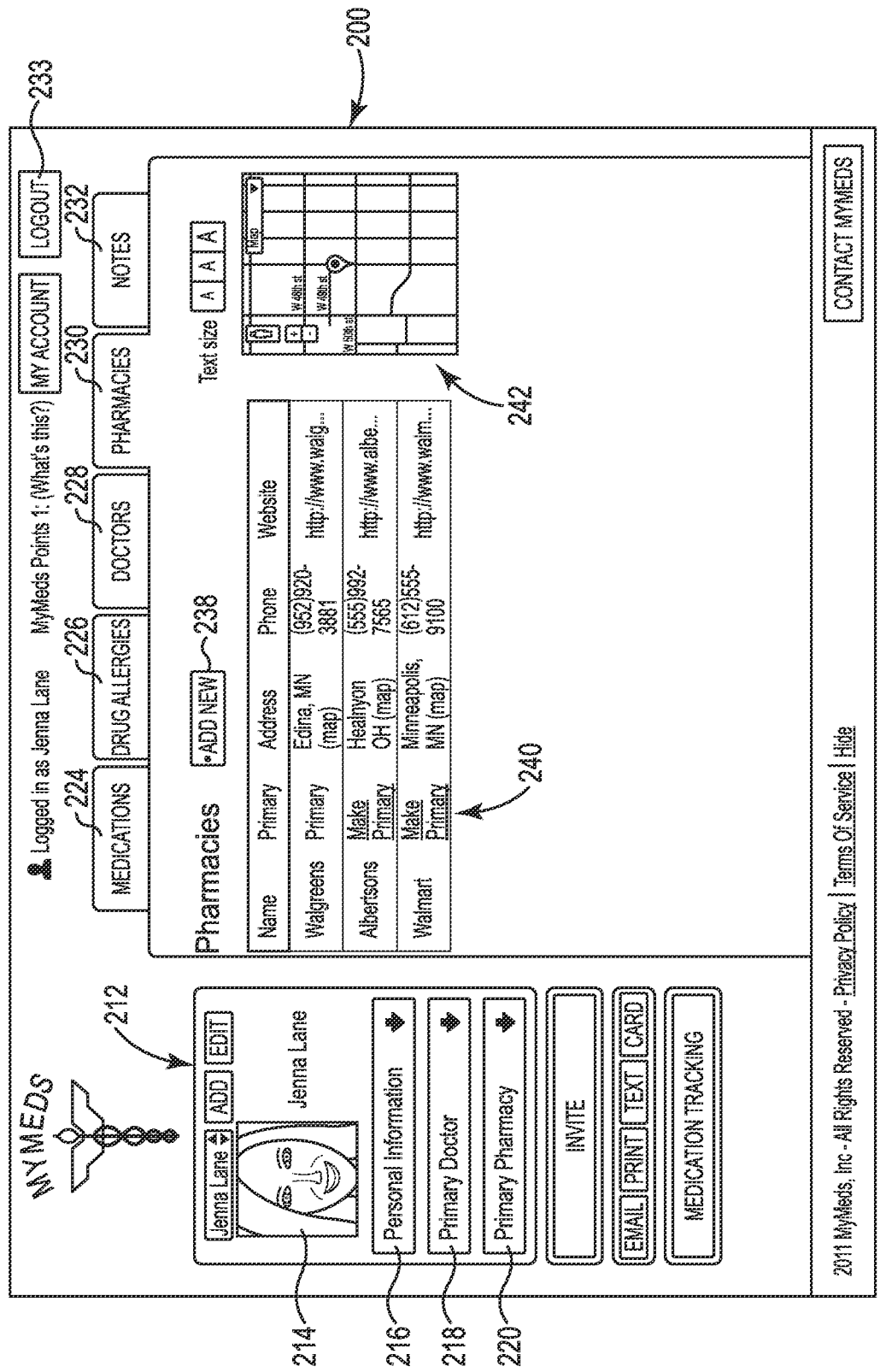
FIGS. 2A-2N are screenshots from an exemplary embodiment of a web-browser based user interface.
Figure 2E:
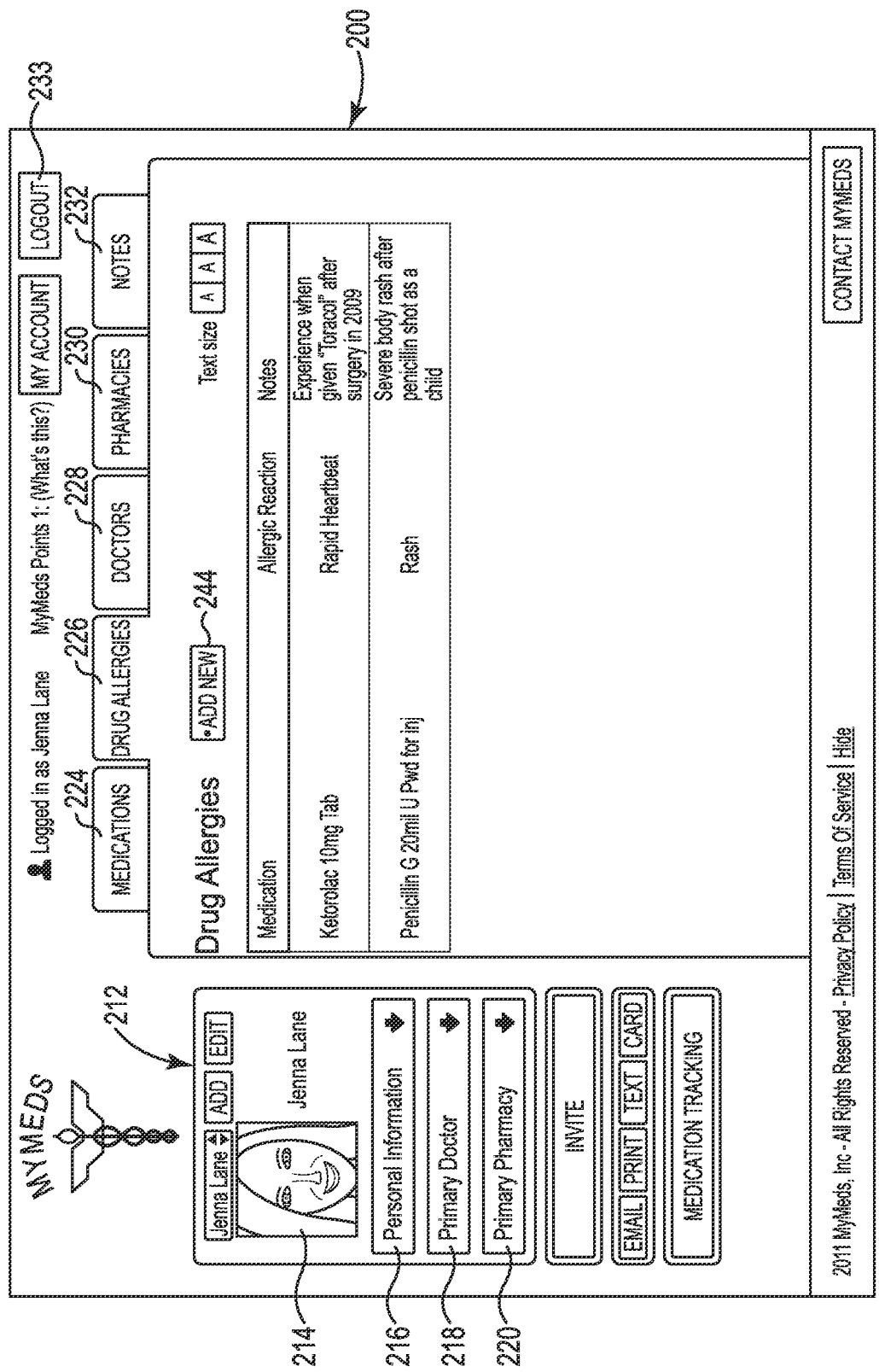
Figure 2F:
Figure 2I:
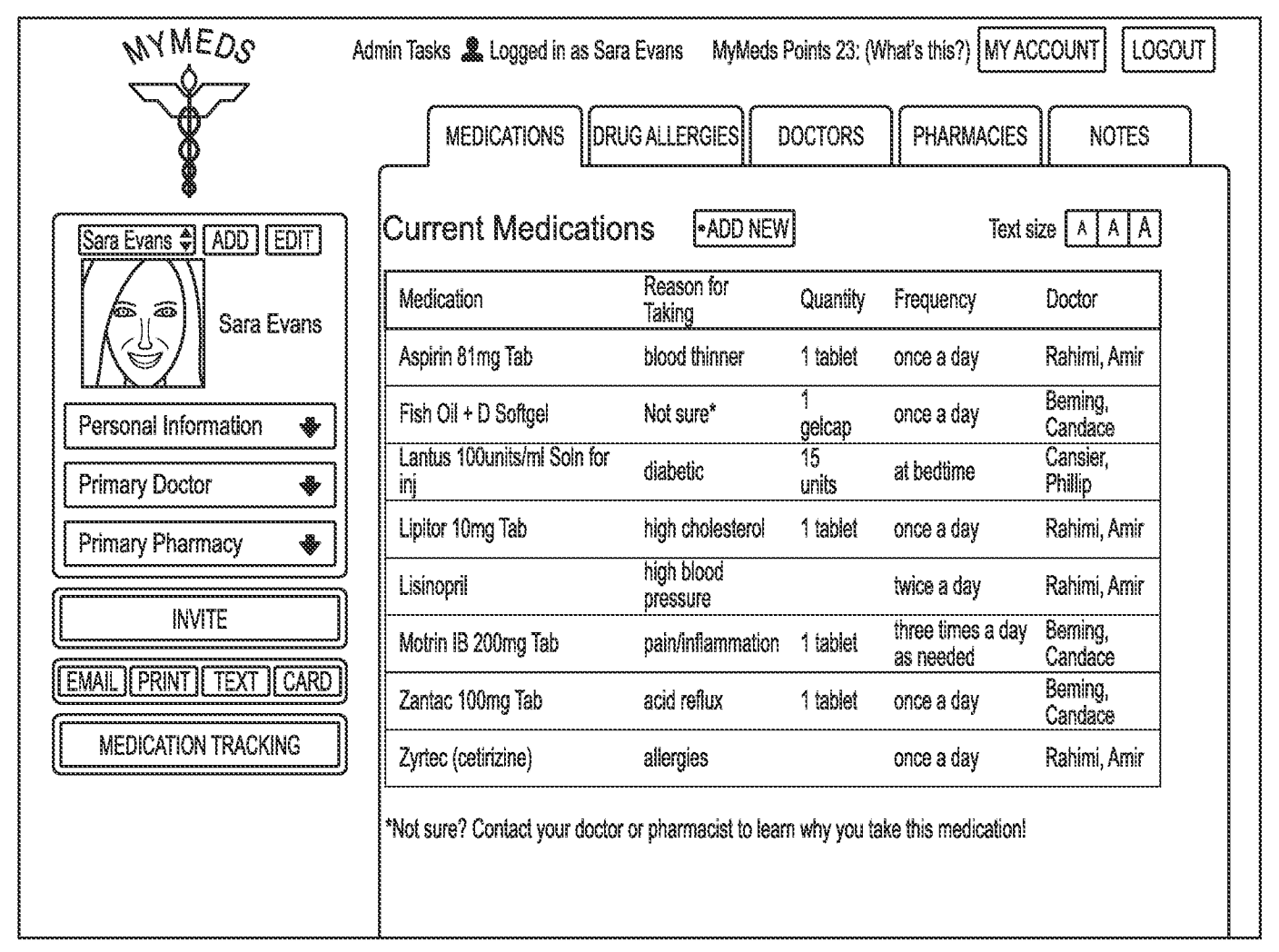
Figure 2K:
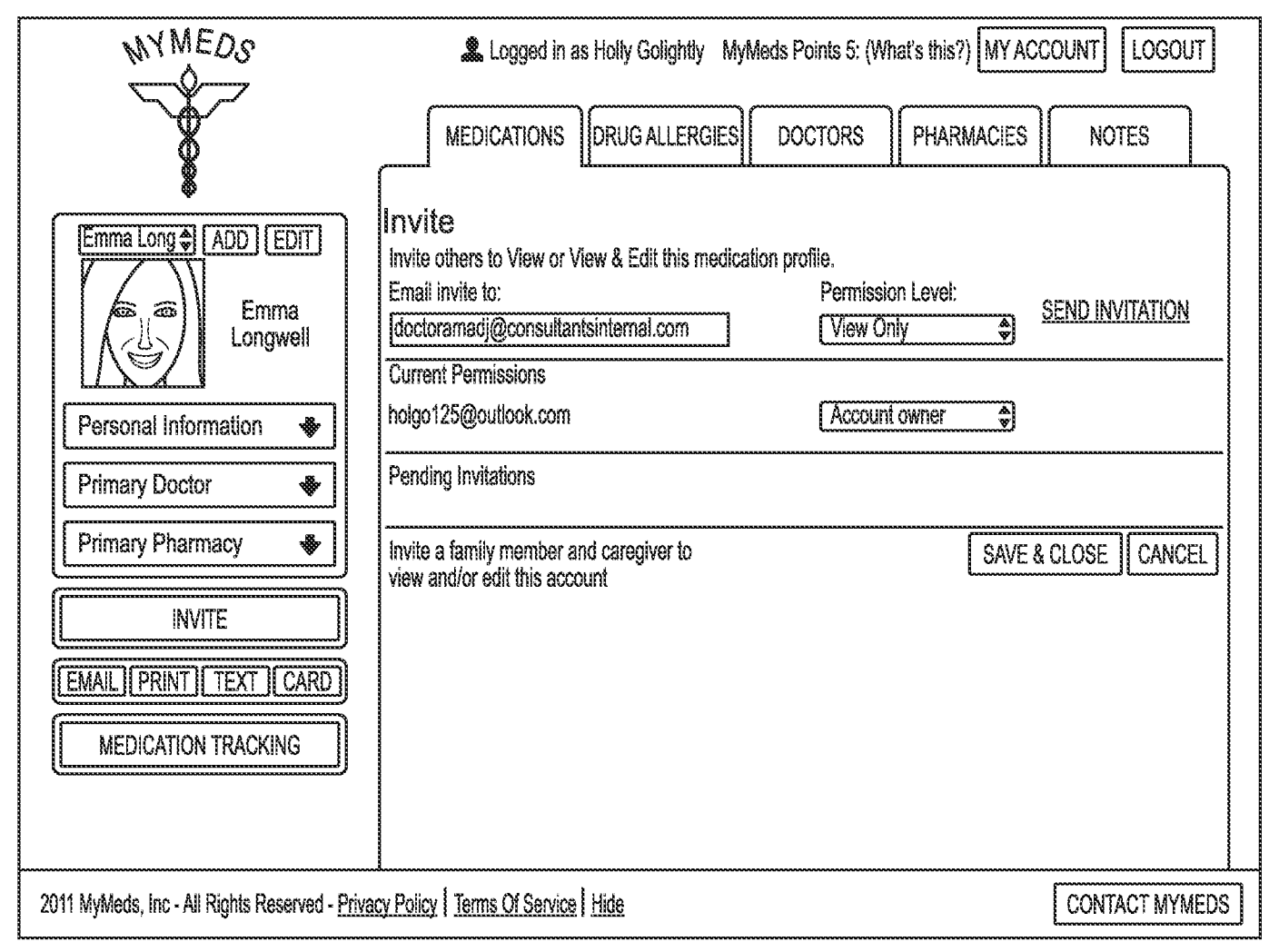
Figure 2L:
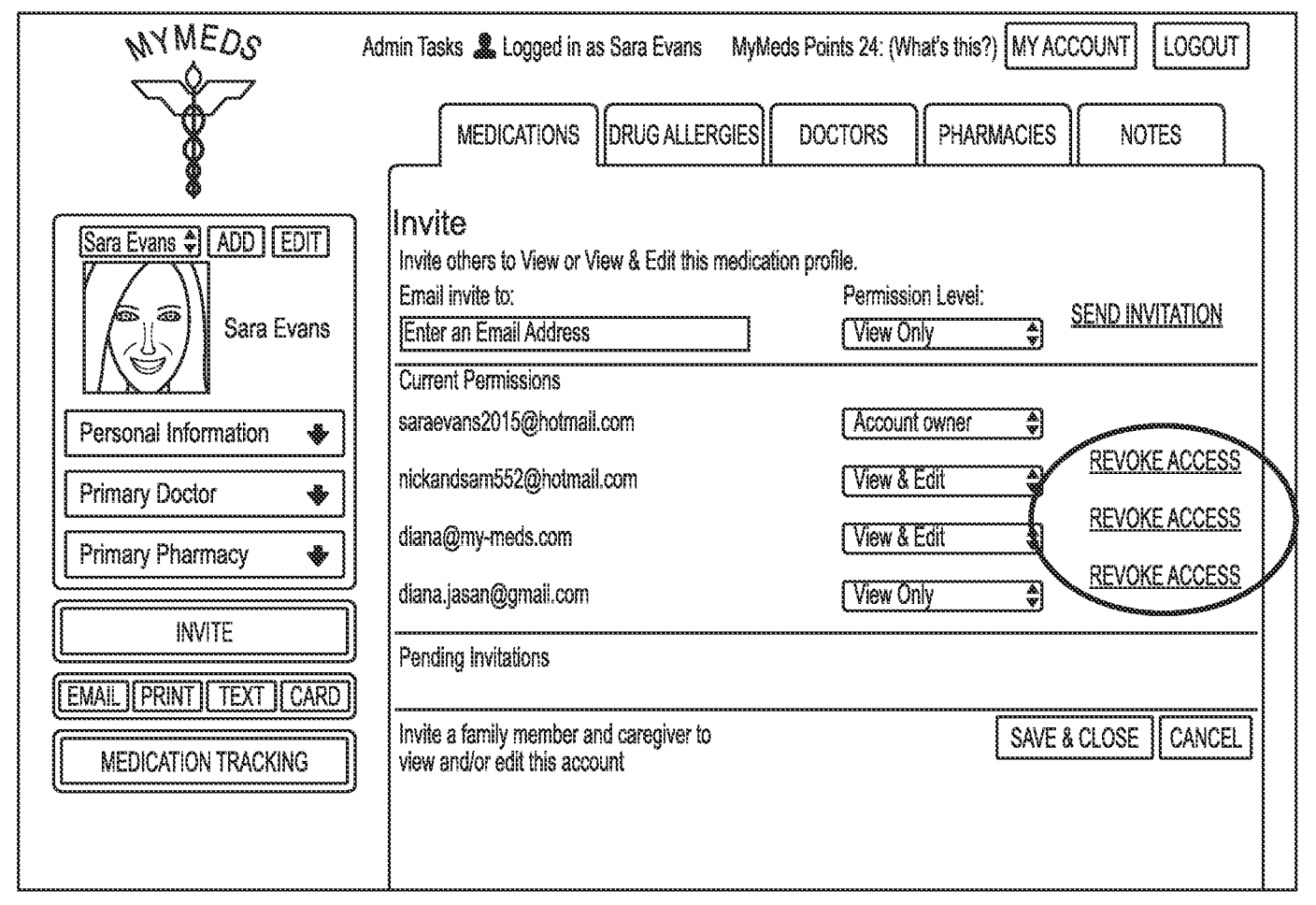
Figure 2M:
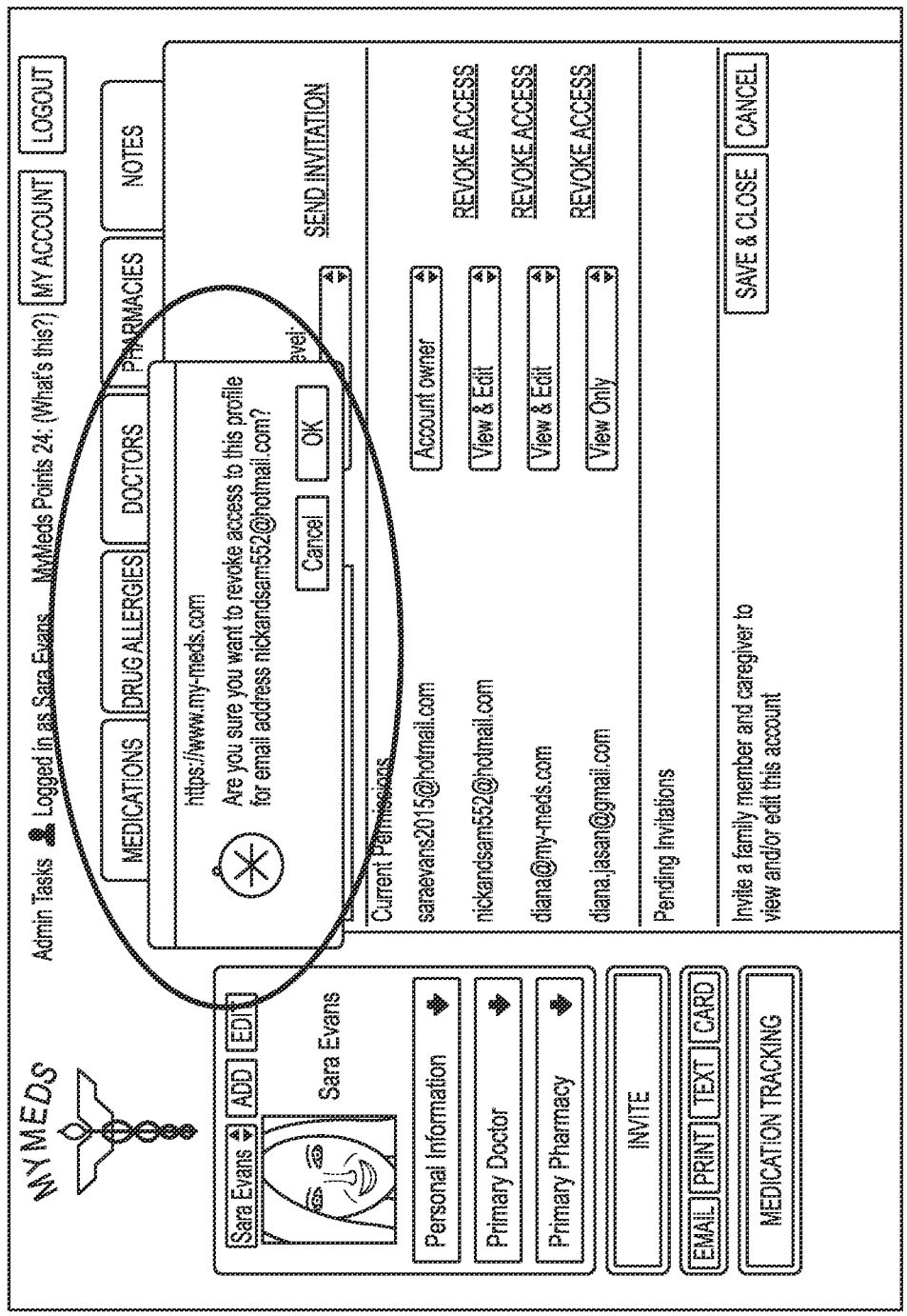
Figure 2N:
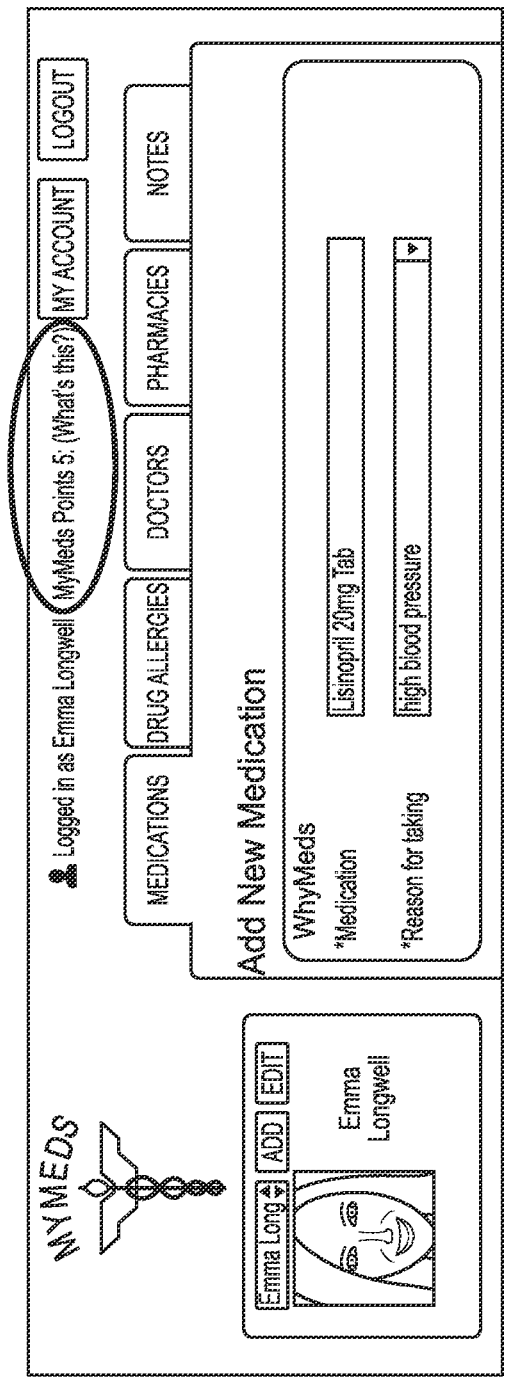
Figure 3A:
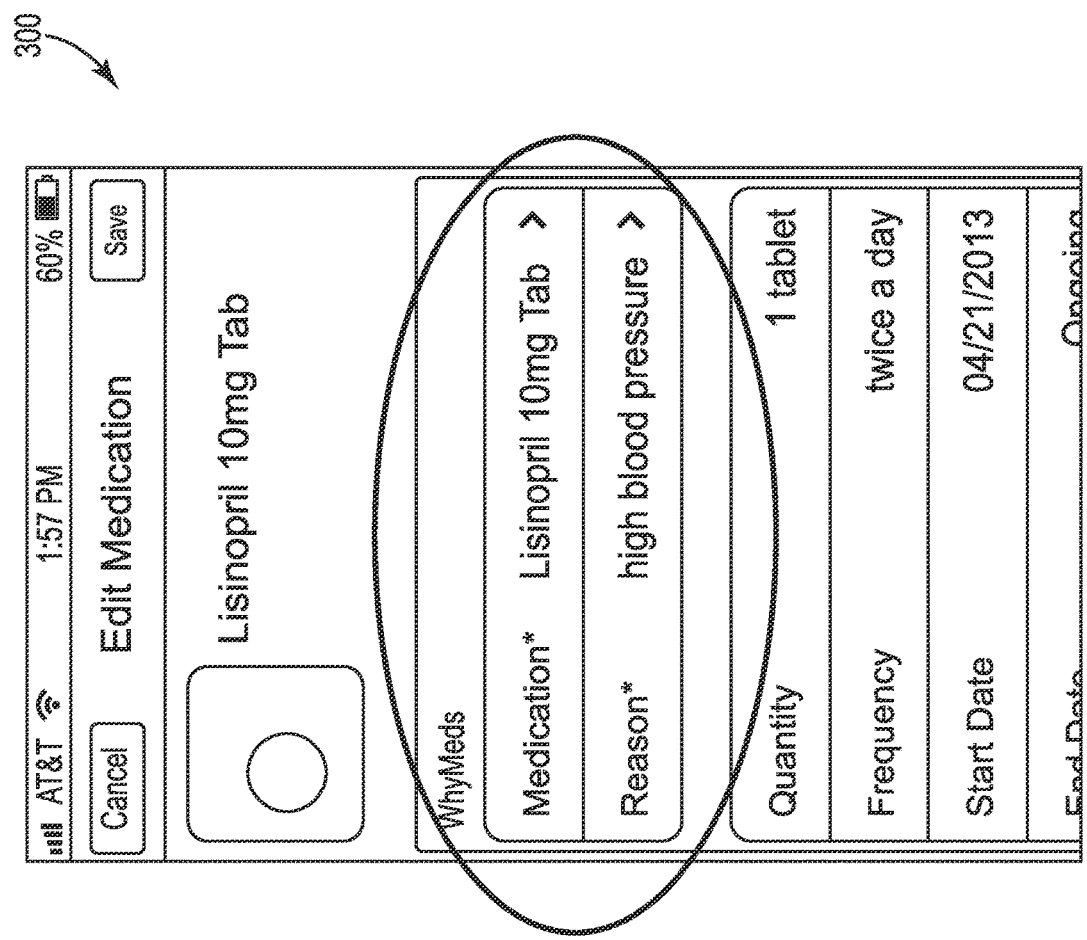
FIGS. 3A-3Q are screenshots from an exemplary embodiment of a mobile application based user interface.
Figure 3B:
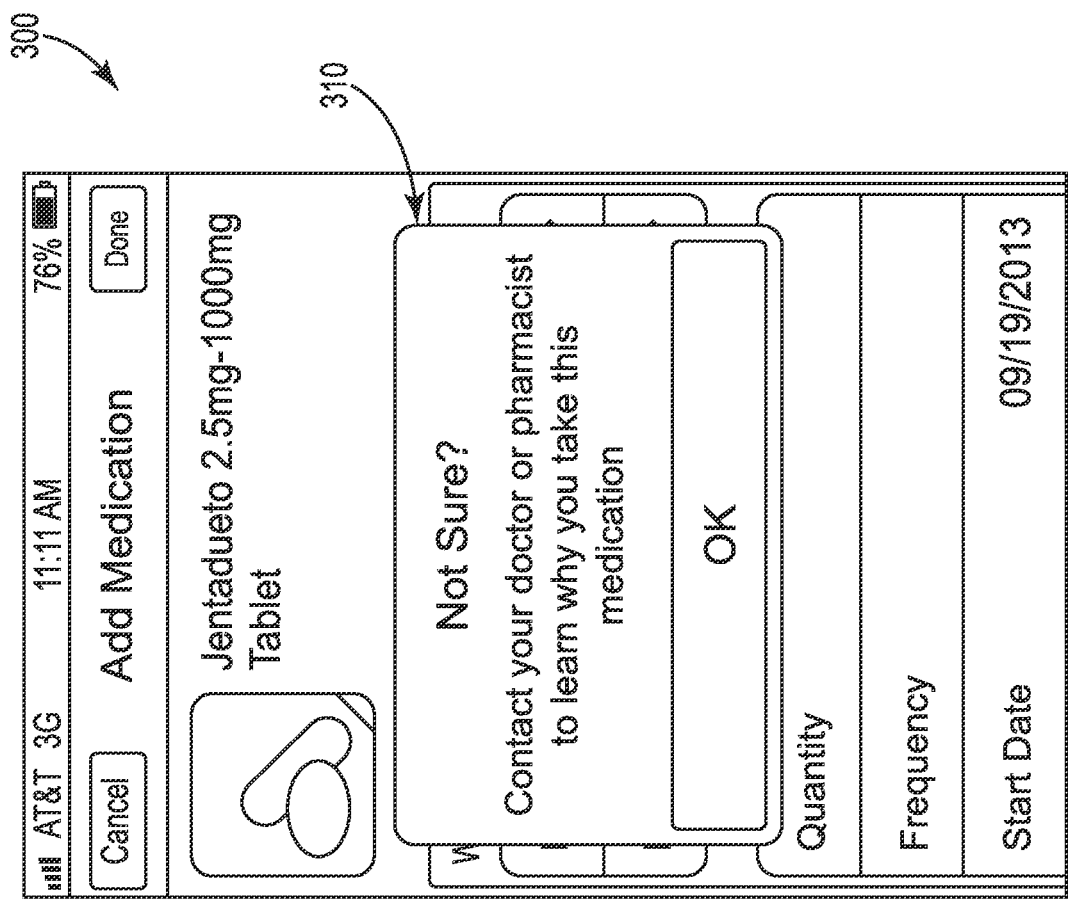
Figure 3C:
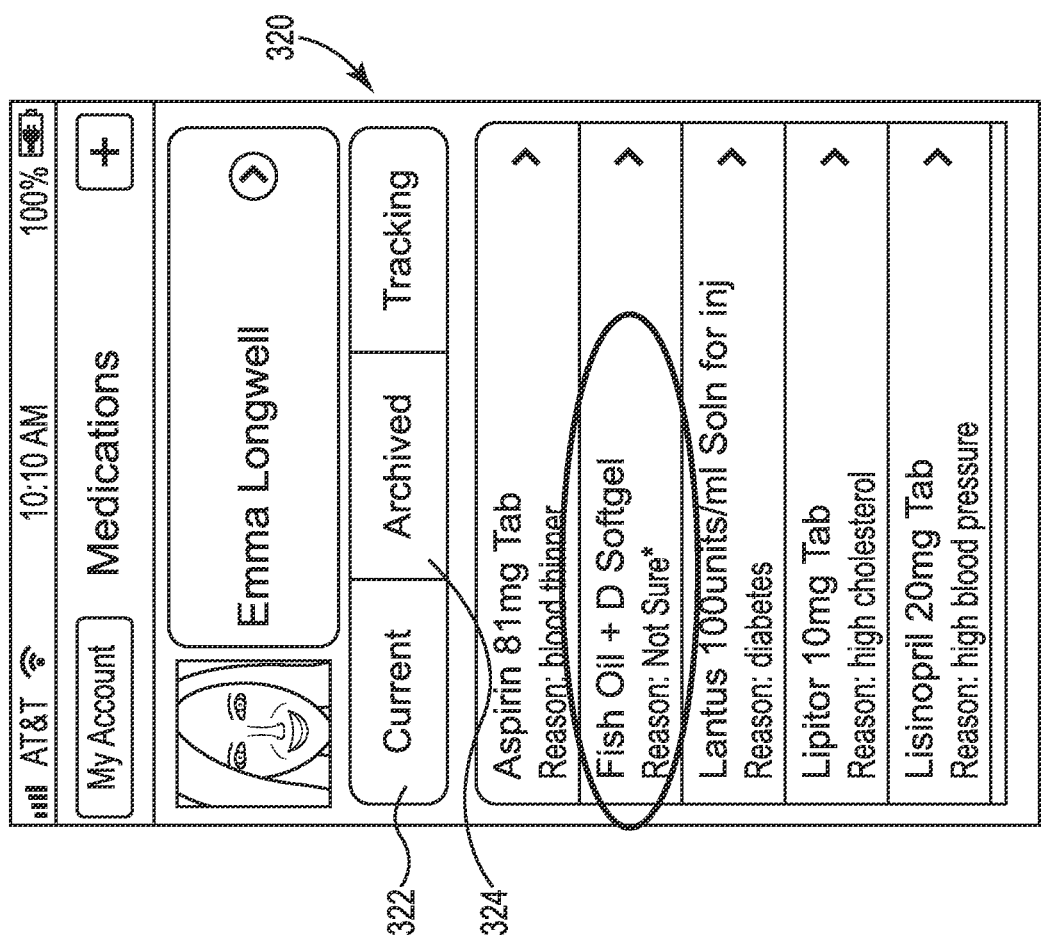
Figure 3E:
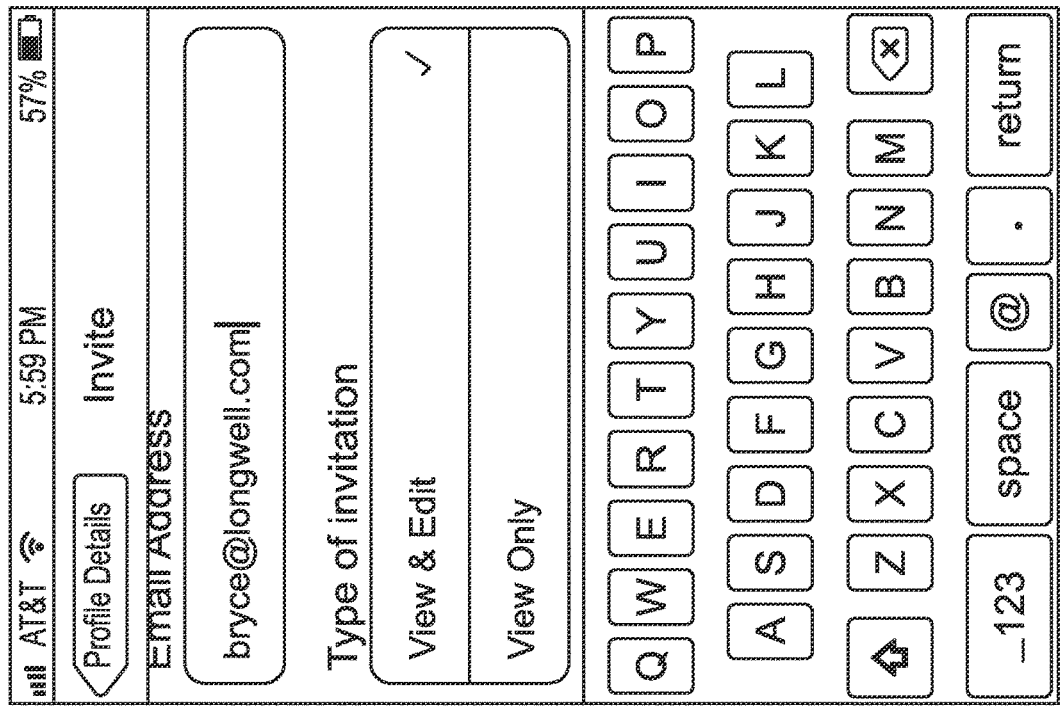
Figure 3D:
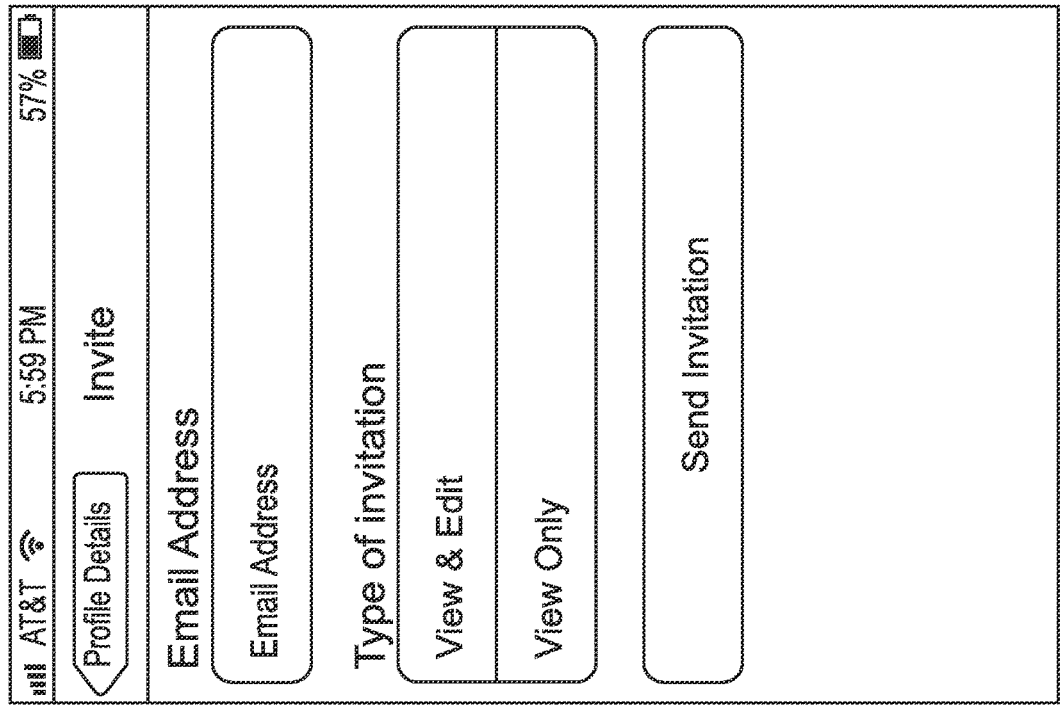
Figure 3F:
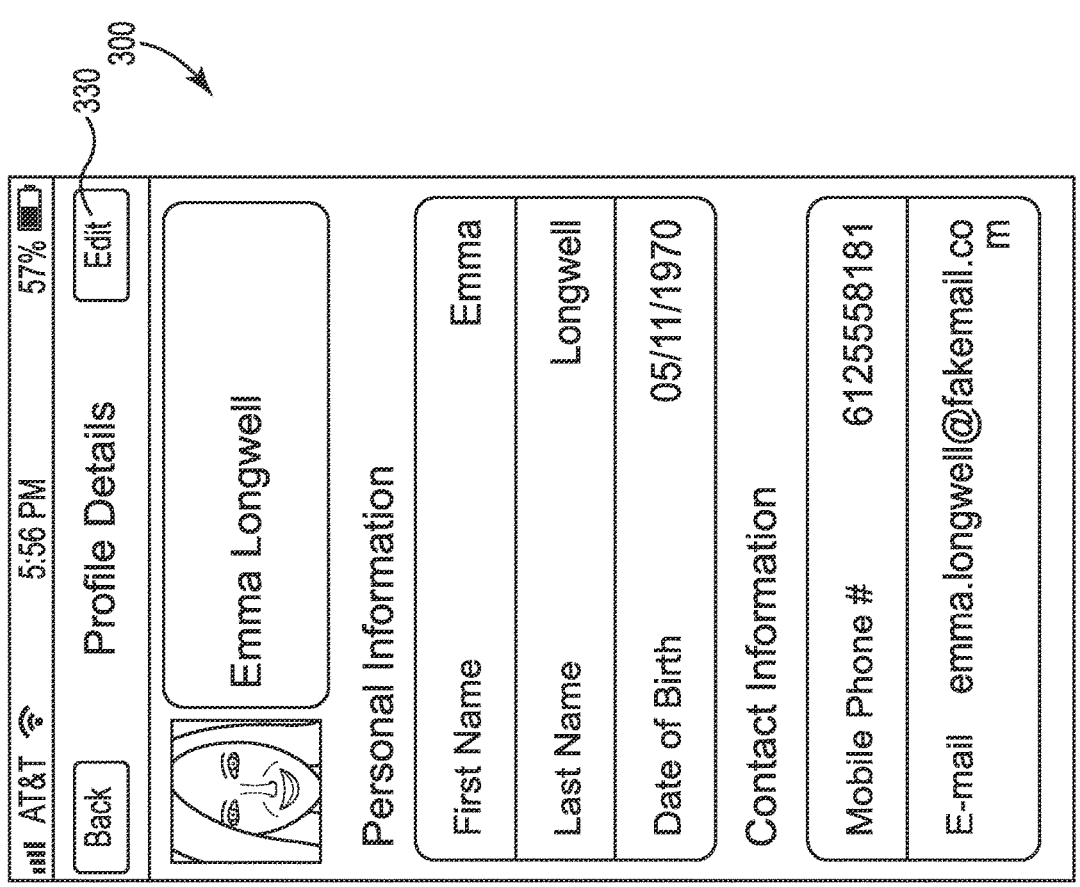
Figure 3I:
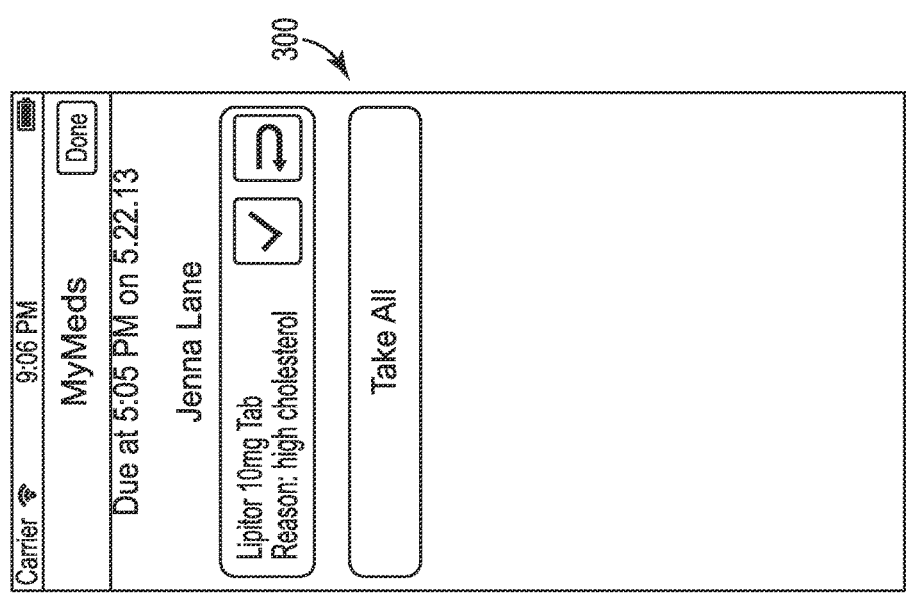
Figure 3H:
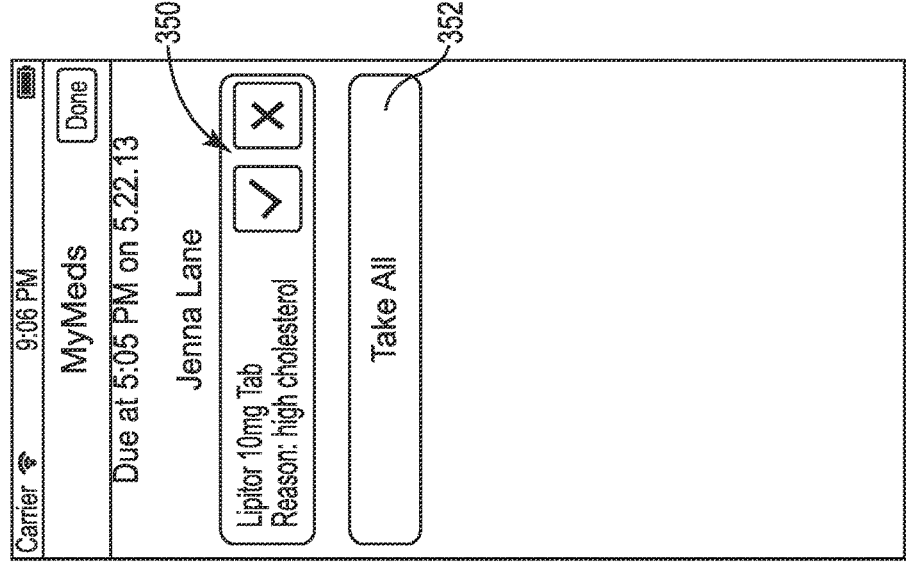
Figure 3G:
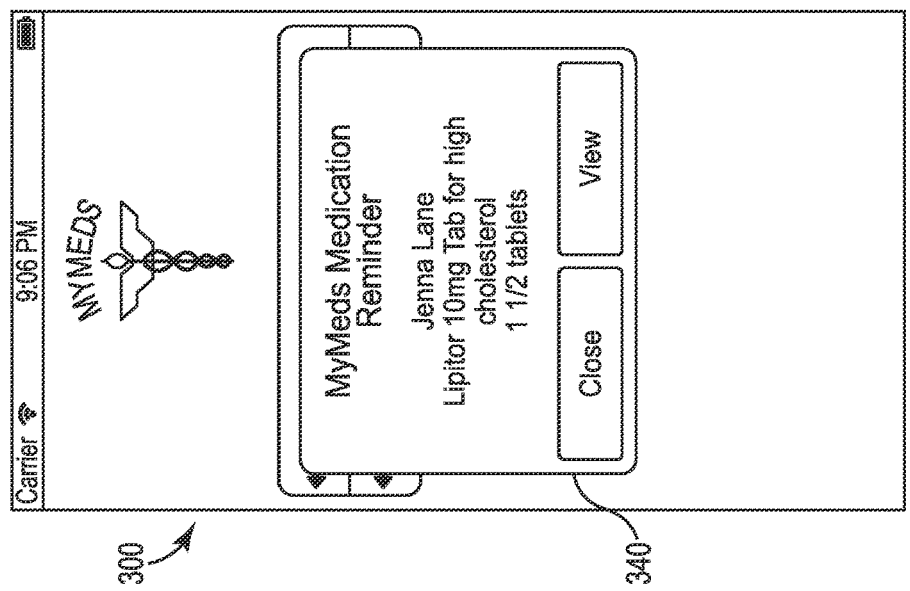
Figures 3J, 3K, 3L:
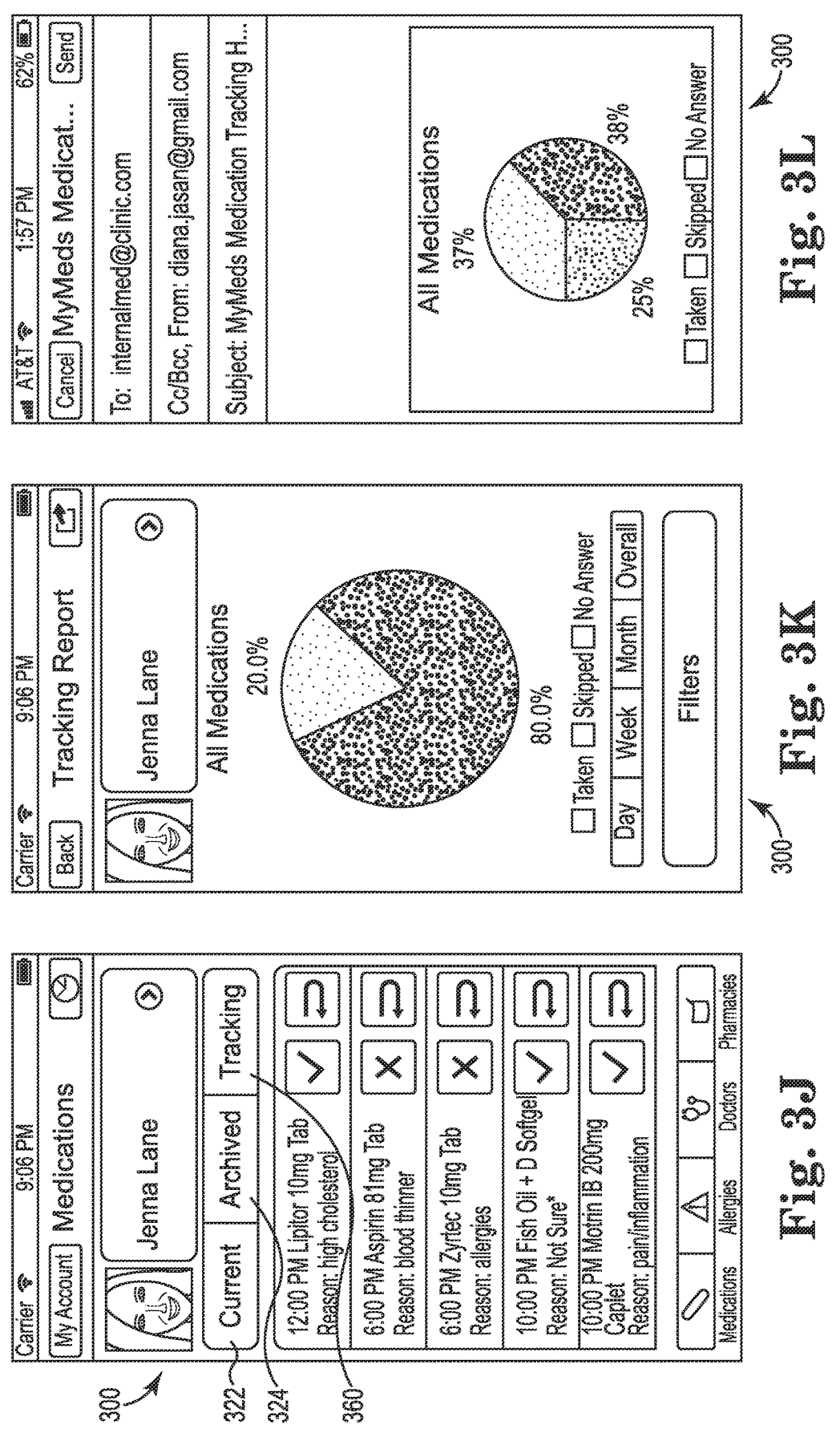
Figure 30:
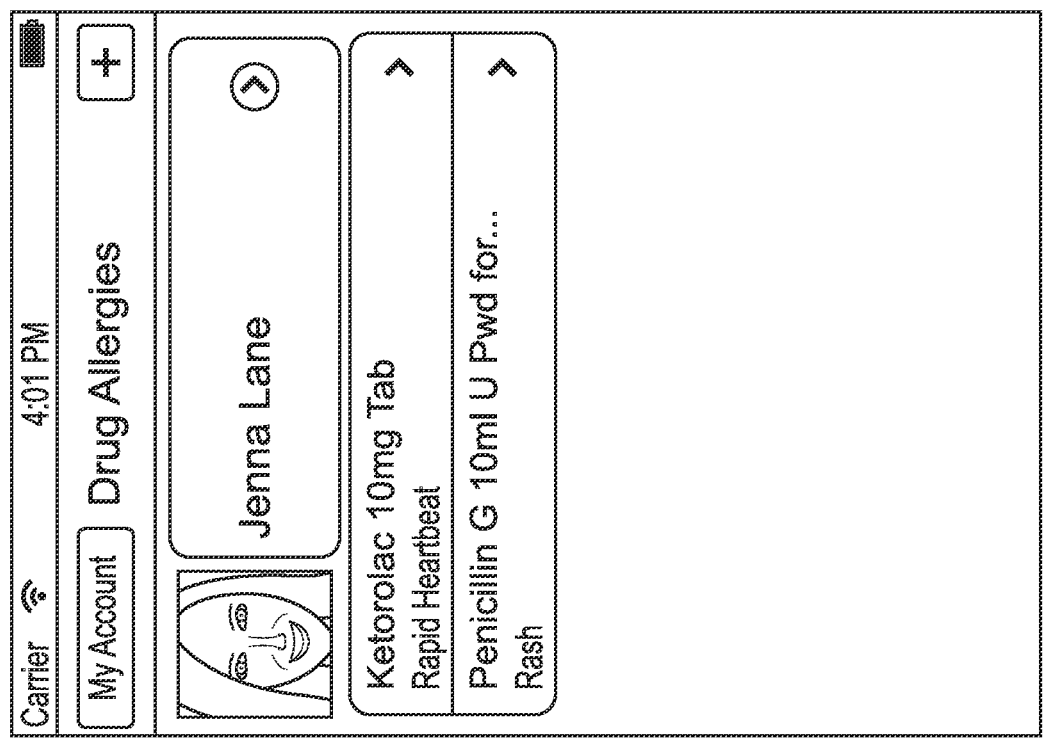
Figure 3Q:
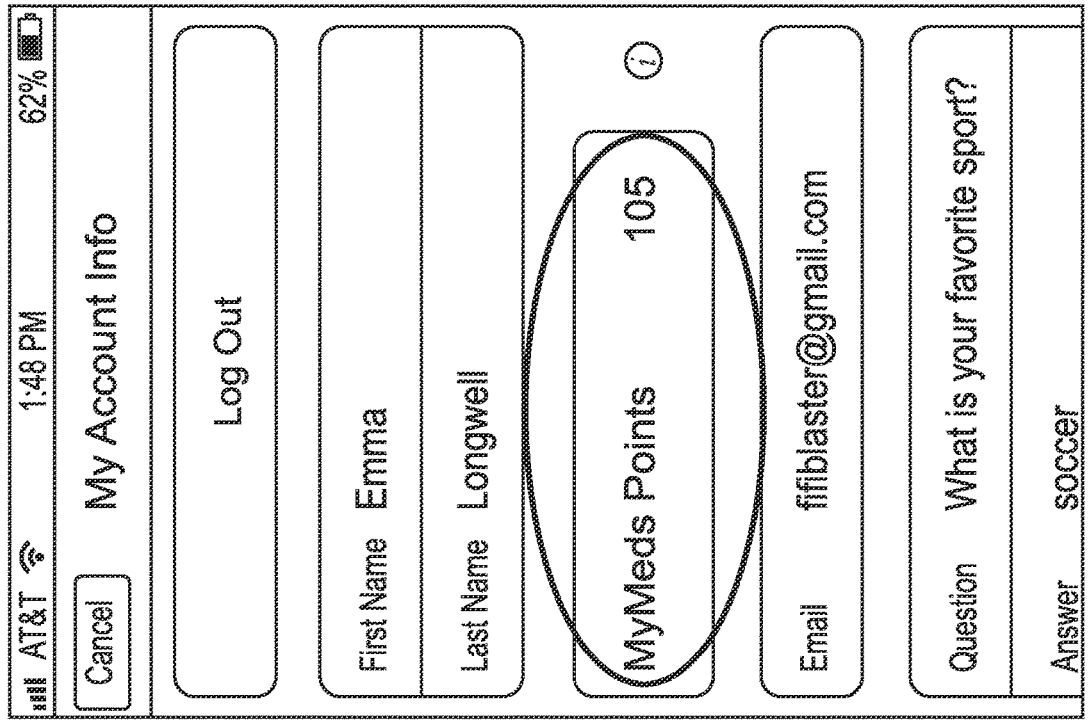

Exemplary embodiments of the user interface include a web-browser based user interface 200 shown in FIGS. 2A-2N and a mobile application based user interface 300 shown FIGS. 3A-3Q. It is contemplated that a user may utilize one or both of the web-browser based user interface 200 and the mobile application based user interface 300 to access the PPS.

FIG. 2A shows an exemplary account creation form 210 for the user interface 200, showing an example of the secure web site user interface page that may assist the user through the registration process discussed above. Here, the user may create a user password as shown in FIG. 2A, whereby the employee may not have access to the user's page without providing that password, in some embodiments. In addition, the user may provide an answer to a particular security question, which may be used for authentication purposes. While passwords and responses to particular security questions are described, other authentication and security methods (such as fingerprints, voice-recognition and/or facial-recognition) are also contemplated and within the spirit of the present disclosure. In at least some embodiments, these same password, security answer, or other authentication method may be used to login into the mobile application-based user interface 300.

As shown in FIG. 2B, the user can create a profile 212, which may include the user's picture 214, personal information 216, primary doctor information, 218 and primary pharmacy information 220. Some of this information may be pre-populated based on the employee's unique ID. Some or all of this profile information may be editable when the user selects the "edit" button 222. The employee/user may be asked to provide additional information such as demographic information, emergency information, or other relevant information. They may also be asked to review and verify the pre-populated information that includes the employee's medication information which may be linked up for viewing based on the employee's unique ID. The user interface may also include a logout feature 233, which allows the user to securely exit the user interface.

As also shown in FIG. 2B, a number of tabs may be provided at the top of the user interface for entering, for example, medications 224, drug allergies 226, doctors 228, pharmacies 230, and notes 232. In the exemplary embodiment shown, the user's profile 212 is shown regardless of which tab 224, 226, 228, 230, 232 the user is presently accessing so that the user can easily verify that the user is currently viewing or editing the correct user's information.

As shown in FIG. 2C, on the tab for doctors 228, the user may add new doctors by selecting the "add new" button 234, including information such as the doctor's name, clinic name, clinic address, phone number and practice specialty. The user has the option of selecting a particular doctor to be listed as their primary doctor, as shown at 236. In at least one embodiment, where the user selects a different doctor to be their primary doctor, the primary doctor information 218 in the user profile 212 automatically updates to reflect the newly selected doctor.

As shown in FIG. 2D, on the tab for pharmacies 230, the user may add new pharmacies by selecting the "add new" button 238, including information such as the pharmacy's name, address, phone number and website. The user has the option of selecting to be listed as their primary doctor, as shown at 240. In at least one embodiment, where the user selects a different pharmacy to be their primary pharmacy, the primary pharmacy information 220 in the user profile 212 automatically updates to reflect the newly selected pharmacy. In at least one embodiment, the user may be able to directly access a map showing the location of the pharmacy (or the doctor's office) and get directions as shown at 242.

As shown in FIG. 2E, on the tab for drug allergies 226, the user may add new allergies by selecting the "add new" button 244, including information such as the name of the medication, the allergic reaction, and notes associated with the allergic reaction.

The user may be asked to enter all medications he or she is currently taking or review and verify the pre-populated medication information. As shown in FIGS. 2F-2I, on the tab for medications 224, the user may add information about new medications, including the name of the medication, the dosage quantity, the frequency of use, dates of use, special instructions for taking the medication, and the prescribing doctor. In at least one embodiment, the doctors listed are pre-populated from the doctor information stored on the tab for doctors. The user may be asked to provide a listing of their medications or it may be pre-populated based on information received through the payer's prescription data as discussed above.

In at least one embodiment, the user may also be asked to provide the reason for use associated with each medication they are taking. In some embodiments, such as the embodiment shown in FIGS. 2F-2I, a user may be asked to select a reason, even by selecting "not sure", in order to save the medication in the user's list of active medications. In some embodiments, such as the embodiment shown in FIG. 2G, the user first selects a medication and then is asked to select a reason for taking from a pre-determined list of reasons pertaining to the selected medication. If the user selects "not sure" in response to the request to tie the reason for use with the medication, a prompt may be provided that instructs the user to see a physician or pharmacist for further information, as shown in FIG. 2H. The user can review their full list of current medications on tab 224, which shows the medication name, the reason for taking, the quantity, the frequency, and the prescribing doctor. In some embodiments, those medications where they are not sure why they are taking a particular medication may be highlighted for instance in red. Further, in some cases, a coding scheme may be used to further inform patients about the medications they are taking. In the example provided above, if a patient/user indicates that they are not sure why they are taking a particular medication, that bottle on the user interface may be colored red, which may indicate that there is something that is unclear or unresolved about that particular medicine. In some cases, medications that are contra-indicated may both turn a certain color, orange for example, which may indicate that the user/patient should discuss these medications with a doctor or pharmacist. In some embodiments, the PPS may include a user-interactive tutorial to help teach users more about the medications they are taking. For example, in one embodiment, a tutorial may help a user tie the name of the medicine to the clinical reason(s) for its use. For example, lisinopril may be taken for high blood pressure, congestive heart failure, or kidney protection. As shown in FIG. 2J, the user is able to print the medication profile, listing all of the current medications and drug allergies, as well as identifying information, in some embodiments.

The user-interface may also have a "my files" application that allows the user to take notes about their doctor visits and keep those notes in one place. For example, if the user interface indicates that two medicines a user is taking are contra-indicated, the bottles may both turn orange and a message may pop-up indicating that the user should speak to a doctor about these medicines. In some cases, the message may automatically be saved in a "notes file" for that medicine, and the message may pop up each time a user logs-in to the system, or at some other pre-determined time. If the user discusses the issue with a professional and is satisfied that taking both medications is ok, the user may include the substance of that consultation in a notes section related to those medicines and may also clear the related message.

In another embodiment, the PPS may include a tutorial that teaches users about the medicines they take by helping them create memory associations between the name of the medicine and the reason(s) for its use. Knowing why one takes a medicine may help increase the likelihood that it will be taken properly. For example, if a person takes a blood pressure medication (e.g. atenolol), but does not know the name, they are less likely to take the medication. If they know they take atenolol, but do not know that it is for blood pressure, they are also less likely to remember to take the medication. If they know that atenolol is a blood pressure medication and their doctor has told them that controlling blood pressure prevents a stroke, the patient makes a memory association about the importance of that medication to their health. This memory association greatly increases the likelihood of taking a medicine as prescribed.

In still other embodiments, the PPS may include, or may also include an invitation feature, such as shown in FIG. 2K. As shown, the invitation feature 250 may be included as part of the user's profile 212. The invitation feature may allow users to invite others to view their secure user interface under a "view" status, or a "view and edit" status in some cases. This feature may allow users to invite others to view their medication profile, or they can invite them to view and edit their medication profile. This may be important in allowing a user's caregiver, for example, to share relevant information and have an ability to co-manage a user's health care. As shown at least in FIGS. 2K-2L, the user has the ability to set viewing permission levels for the third parties as shown at 252. In at least the embodiment shown in FIGS. 2K-2L, the user can revoke any access provided to others at any time as shown at 254. As shown in FIG. 2M, the user may be subject to a popup window 260 requesting the user to verify that the user wants to revoke access to the particular user profile.

In some embodiments, claims information can be used to send notifications for refill requests to the user. For example, if the medication had 30 tablets when the prescription is filled, the system may send an auto-refill reminder with pharmacy information to the user 7-10 days, for example, beforehand so that the user can order a refill before the prescription runs out. In some cases, the user may determine how soon in advance a reminder(s) is sent prior to a prescription running out. This system may be used for prescription medications, over-the-counter medications, vitamins, and/or herbal supplements, for example.

In some embodiments, as shown in FIG. 2N, the system may include a rewards feature for the provider or source (e.g. employer, insurer, etc.) to incentivize users to use the system. The rewards feature may calculate points for various tasks (e.g. signing up, creating an account, setting alarms, taking medicines, etc.) and tabulate the points. The points may be shown on the user interface as shown in FIG. 2N at 270. In some embodiments, users may redeem the tabulated points for incentive products such as items or gift certificates.

As mentioned above with respect to the web-browser based user interface 200, the mobile application user interface 300 may include many of the same features and functionalities as the web-browser based user interface 200. As shown in FIG. 3A, the mobile application user interface 300 can display each medication, and the user can select or edit the medication and provide a reason for taking the medication. In at least one embodiment, as shown in FIG. 3B, if the user selects "not sure" as the reason, the mobile application user interface 300 displays a prompt 310 or other notification for the user to contact his or her doctor or pharmacist to learn why you take this medication. In at least one embodiment, as shown in FIG. 3C, in the user's list of medications 320, the name of the medication may be displayed along with the reason for taking the medication. In some embodiments, the user is able to store information related to the medications that the user is currently taking as well as prior taken medications. In at least one embodiment shown in FIG. 3C, these are stored under separate tabs, such as a "current" tab 322 and an "archived" tab 324. In some embodiments, such as the embodiment shown in FIGS. 3D-3E, the mobile application user interface includes the ability for the user to invite others to the user's information page(s). The user and/or another entity may select the permission level of the other user to edit and/or view the user's information. In some embodiments, such as the embodiment shown in FIG. 3F, the user can view the user profile and can edit the profile. In at least one embodiment, the user can select an "edit" button 330 to modify the information. In some embodiments, the level of "edit" access may be selected by the user such that in some cases all information may be edited, while in other cases, only selected information may be edited by the invited guest. In other embodiments, however, a guest may only be able to view a user's profile, but not edit the profile or profile information.

In some embodiments, as shown in FIGS. 3G-3J, the mobile application user interface 300 provides reminder notifications 340 or other messages to remind the person that a particular medication needs to be administered at a particular time. As shown in FIGS. 3G-3H, the mobile application user interface allows the user to either delete the reminder or affirm that the medication was taken, as shown at 350. In some embodiments, as shown in FIGS. 3G-3H, the user can also affirm that it has taken multiple medications by selecting the "take all" button 352. The mobile application user interface 300 thus records if and when the user has taken a particular medication. As shown in FIG. 3J, the user can review what medications were taken by selecting the "tracking" feature 360, which displays the most recently taken medication and the time it was taken, or in cases where the medication was not taken but should have been, it displays that information also.

Figure 3P:
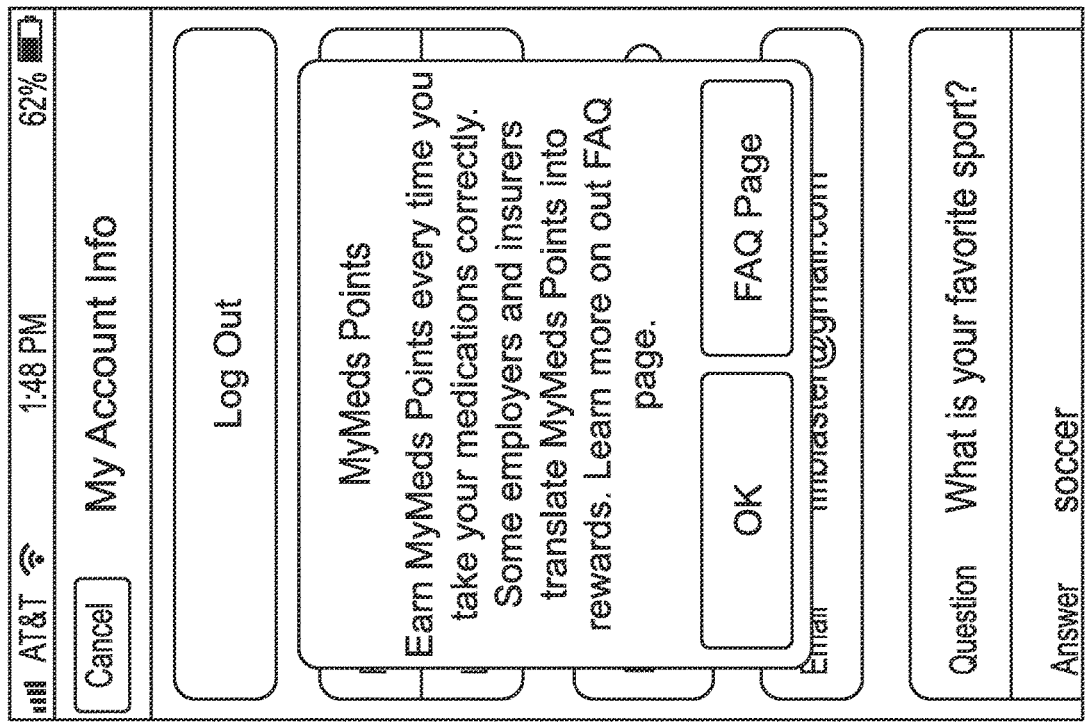

In addition, the mobile application user interface 300 can provide tracking reports for taken and skipped medications, which can be displayed based on one or more parameters such as day, week, month or overall, as shown in FIG. 3K and can be e-mailed or otherwise sent to another person as shown in FIG. 3L. Like the web-browser based user interface 200, the mobile application user interface 300 also can provide doctor information as shown in FIG. 3M, pharmacy information as shown in FIG. 3N, and drug allergy information as shown in FIG. 3O. This information may be editable through the mobile application user interface 300, or the user may have to login to the web-browser based user interface 200 in order to edit the information. Like the web-browser based user interface 200, the mobile application user interface 300 also can include a rewards feature, which may calculate points for various tasks completed (e.g. signing up, creating an account, setting alarms, taking medicines, etc.), tabulate the points, and display them as shown in FIGS. 3P-3Q. It will be understood that while a particular feature may have been described herein with regard to the web-based version or the mobile application version, any of the features described may be combined or added to any of the embodiments of the present disclosure.

For purposes of this disclosure, any system described herein may include any instrumentality or aggregate of instrumentalities operable to compute, calculate, determine, classify, process, transmit, receive, retrieve, originate, switch, store, display, communicate, manifest, detect, record, reproduce, handle, or utilize any form of information, intelligence, or data for business, scientific, control, or other purposes. For example, a system or any portion thereof may be a personal computer (e.g., desktop or laptop), tablet computer, mobile device (e.g., personal digital assistant (PDA) or smart phone), server (e.g., blade server or rack server), a network storage device, or any other suitable device or combination of devices and may vary in size, shape, performance, functionality, and price. A system may include random access memory (RAM), one or more processing resources such as a central processing unit (CPU) or hardware or software control logic, ROM, and/or other types of nonvolatile memory. Additional components of a system may include one or more disk drives or one or more mass storage devices, one or more network ports for communicating with external devices as well as various input and output (I/O) devices, such as a keyboard, a mouse, touchscreen and/or a video display. Mass storage devices may include, but are not limited to, a hard disk drive, floppy disk drive, CD-ROM drive, smart drive, flash drive, or other types of non-volatile data storage, a plurality of storage devices, or any combination of storage devices. A system may include what is referred to as a user interface, which may generally include a display, mouse or other cursor control device, keyboard, button, touchpad, touch screen, microphone, camera, video recorder, speaker, LED, light, joystick, switch, buzzer, bell, and/or other user input/output device for communicating with one or more users or for entering information into the system. Output devices may include any type of device for presenting information to a user, including but not limited to, a computer monitor, flat-screen display, or other visual display, a printer, and/or speakers or any other device for providing information in audio form, such as a telephone, a plurality of output devices, or any combination of output devices. A system may also include one or more buses operable to transmit communications between the various hardware components.

One or more programs or applications, such as a web browser, and/or other applications may be stored in one or more of the system data storage devices. Programs or applications may be loaded in part or in whole into a main memory or processor during execution by the processor. One or more processors may execute applications or programs to run systems or methods of the present disclosure, or portions thereof, stored as executable programs or program code in the memory, or received from the Internet or other network. Any commercial or freeware web browser or other application capable of retrieving content from a network and displaying pages or screens may be used. In some embodiments, a customized application may be used to access, display, and update information.

Hardware and software components of the present disclosure, as discussed herein, may be integral portions of a single computer or server or may be connected parts of a computer network. The hardware and software components may be located within a single location or, in other embodiments, portions of the hardware and software components may be divided among a plurality of locations and connected directly or through a global computer information network, such as the Internet and/or the "cloud."

As will be appreciated by one of skill in the art, the various embodiments of the present disclosure may be embodied as a method (including, for example, a computer-implemented process, a business process, and/or any other process), apparatus (including, for example, a system, machine, device, computer program product, and/or the like), or a combination of the foregoing. Accordingly, embodiments of the present disclosure may take the form of an entirely hardware embodiment, an entirely software embodiment (including firmware, middleware, microcode, hardware description languages, etc.), or an embodiment combining software and hardware aspects. Furthermore, embodiments of the present disclosure may take the form of a computer program product on a computer-readable medium or computer-readable storage medium, having computer-executable program code embodied in the medium, that define processes or methods described herein. A processor or processors may perform the necessary tasks defined by the computer-executable program code. Computer-executable program code for carrying out operations of embodiments of the present disclosure may be written in an object oriented, scripted or unscripted programming language such as Java, Perl, PHP, Visual Basic, Smalltalk, C++, or the like. However, the computer program code for carrying out operations of embodiments of the present disclosure may also be written in conventional procedural programming languages, such as the C programming language or similar programming languages. A code segment may represent a procedure, a function, a subprogram, a program, a routine, a subroutine, a module, an object, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

In the context of this document, a computer readable medium may be any medium that can contain, store, communicate, or transport the program for use by or in connection with the systems disclosed herein. The computer-executable program code may be transmitted using any appropriate medium, including but not limited to the Internet, optical fiber cable, radio frequency (RF) signals or other wireless signals, or other mediums. The computer readable medium may be, for example but is not limited to, an electronic, magnetic, optical, electromagnetic, infrared, or semiconductor system, apparatus, or device. More specific examples of suitable computer readable medium include, but are not limited to, an electrical connection having one or more wires or a tangible storage medium such as a portable computer diskette, a hard disk, a random access memory (RAM), a read-only memory (ROM), an erasable programmable read-only memory (EPROM or Flash memory), a compact disc read-only memory (CD-ROM), or other optical or magnetic storage device. Computer-readable media includes, but is not to be confused with, computer-readable storage medium, which is intended to cover all physical, non-transitory, or similar embodiments of computer-readable media.

Various embodiments of the present disclosure may be described herein with reference to flowchart illustrations and/or block diagrams of methods, apparatus (systems), and computer program products. It is understood that each block of the flowchart illustrations and/or block diagrams, and/or combinations of blocks in the flowchart illustrations and/or block diagrams, can be implemented by computer-executable program code portions. These computer-executable program code portions may be provided to a processor of a general purpose computer, special purpose computer, or other programmable data processing apparatus to produce a particular machine, such that the code portions, which execute via the processor of the computer or other programmable data processing apparatus, create mechanisms for implementing the functions/acts specified in the flowchart and/or block diagram block or blocks. Alternatively, computer program implemented steps or acts may be combined with operator or human implemented steps or acts in order to carry out an embodiment of the invention.

Additionally, although a flowchart may illustrate a method as a sequential process, many of the operations in the flowcharts illustrated herein can be performed in parallel or concurrently. In addition, the order of the method steps illustrated in a flowchart may be rearranged for some embodiments. Similarly, a method illustrated in a flow chart could have additional steps not included therein or fewer steps than those shown. A method step may correspond to a method, a function, a procedure, a subroutine, a subprogram, etc.

As used herein, the terms "substantially" or "generally" refer to the complete or nearly complete extent or degree of an action, characteristic, property, state, structure, item, or result. For example, an object that is "substantially" or "generally" enclosed would mean that the object is either completely enclosed or nearly completely enclosed. The exact allowable degree of deviation from absolute completeness may in some cases depend on the specific context. However, generally speaking, the nearness of completion will be so as to have generally the same overall result as if absolute and total completion were obtained. The use of "substantially" or "generally" is equally applicable when used in a negative connotation to refer to the complete or near complete lack of an action, characteristic, property, state, structure, item, or result. For example, an element, combination, embodiment, or composition that is "substantially free of" or "generally free of" an ingredient or element may still actually contain such item as long as there is generally no measurable effect thereof.

In the foregoing description various embodiments of the present disclosure have been presented for the purpose of illustration and description. They are not intended to be exhaustive or to limit the invention to the precise form disclosed. Obvious modifications or variations are possible in light of the above teachings. The various embodiments were chosen and described to provide the best illustration of the principals of the disclosure and their practical application, and to enable one of ordinary skill in the art to utilize the various embodiments with various modifications as are suited to the particular use contemplated. All such modifications and variations are within the scope of the present disclosure as determined by the appended claims when interpreted in accordance with the breadth they are fairly, legally, and equitably entitled.

What is claimed is:

1. A computer-based method for managing medication data for a plurality of users, the method comprising:
   obtaining, using a portal provider system comprising a database, medication data associated with a plurality of users through a secure document extraction process and in real time from a medication information source, wherein the medication data comprises the users' prescribed, dispensed, and claimed medicines;
   storing, using the portal provider system, the medication data in the database in a non-transitory computer readable media;
   providing, through a secure patient portal comprising a web-based user interface, access for a respective user of the plurality of users to the medication data associated with that respective user from the database;
   for each of the plurality of users, pre-populating, using the portal provider system, the secure patient portal with the medication data associated with each of the plurality of users from the database;
   sending, using the portal provider system, an invitation to one or more of the plurality of users, the invitation comprising a registration link for the secure patient portal to enable the one or more of the plurality of users to securely register for the secure patient portal by creating a unique login and password;
   once a respective one of the plurality of users creates a unique login and password, receiving information from the respective one of the plurality of users and completing, using the portal provider system, a user profile for the respective one of the plurality of users based on the received information; and
   providing, through the secure patient portal, to the respective one of the plurality of users, a user-interactive computer-implemented tutorial, wherein, using computer executable instructions, the tutorial provides information to the respective one of the plurality of users to associate the name of a medication from the medication data associated with that respective one of the plurality of users with the clinical condition for which the medication was prescribed to increase a likelihood of the respective one of the plurality of users taking the medication as prescribed.

2. The method of claim 1, wherein the plurality of users are employees of an employer.

3. The method of claim 1, wherein the medication information source is a pharmacy benefit manager, a healthcare system, an electronic prescription network, or a pharmacy.

4. The method of claim 1, wherein the medication data comprises prescription medicines, over-the-counter medicines, and herbal supplements.

5. The method of claim 1, wherein the medication data is updated continuously in real time.

6. The method of claim 1, further comprising providing a third party with secure access to the respective one of the plurality of users medication data after receiving an indication that the respective one of the plurality of users wishes to grant access to the third party.

7. The method of claim 6, wherein the access is view-only access.

8. The method of claim 6, wherein the access is view-and-edit access.

9. The method of claim 6, further comprising providing the respective one of the plurality of users with alerts indicating when the one or more medications prescribed, dispensed, or claimed by the respective one of the plurality of users need to be refilled.

10. The method of claim 1, further comprising providing plurality of users with an ability to designate a preferred pharmacy from the pharmacy directory.

11. The method of claim 1, wherein the secure patient portal is a web-based portal or a mobile-based portal.

12. The method of claim 1, wherein the medication data is received from a pharmacy benefit manager for an employer or a health plan.

13. The method of claim 1, wherein the plurality of users are members of a health plan.

14. The method of claim 1, further comprising requesting medication data for the respective one of the plurality of users on an on-demand basis.

15. The method of claim 6, wherein the third party is the respective one of the plurality of users caregiver.

16. The method of claim 6, wherein the third party is the user's clinical care team.

17. The method of claim 1, further comprising providing a computer-implemented rewards system, whereby the respective one of the plurality of users is granted reward points for completing the tutorial.

18. A non-transitory computer-readable storage medium encoded with instructions that, when executed by one or more processors, cause the one or more processors to perform operations comprising:
   obtaining medication data associated with a plurality of users through a secure document extraction process and in real time from a medication information source, wherein the medication data comprises the users' prescribed, dispensed, and claimed medicines;
   storing the medication data in a database in a non-transitory computer readable media;
   providing, through a secure patient portal comprising a web-based user interface, access for a respective user of the plurality of users to the medication data associated with that respective user from the database;

for each of the plurality of users, pre-populating the secure patient portal with the medication data associated with each of the plurality of users from the database;

sending an invitation to one or more of the plurality of users, the invitation comprising a registration link for the secure patient portal, to enable the one or more of the plurality of users to securely register for the secure patient portal by creating a unique login and password;

once a respective one of the plurality of users creates a unique login and password, receiving information from the respective one of the plurality of users and completing a user profile for the respective one of the plurality of users based on the received information; and providing, through the secure patient portal, to the respective one of the plurality of users, a user-interactive computer-implemented tutorial, wherein, using computer executable instructions, the tutorial provides information to the respective one of the plurality of users to associate the name of a medication from the medication data associated with that respective one of the plurality of users with the clinical condition for which the medication was prescribed to increase a likelihood of the respective one of the plurality of users taking the medication as prescribed.

* * * * *